(12) United States Patent
Yokoyama et al.

(10) Patent No.: US 6,419,962 B1
(45) Date of Patent: *Jul. 16, 2002

(54) EXTERNAL SKIN TREATMENT COMPOSITION

(75) Inventors: Mineyuki Yokoyama; Hiroyuki Tsukada; Tetsuya Sakai; Shoko Yamaguchi; Yumiko Suzuki; Yasukazu Nakayama, all of Yokohama; Hiroaki Yasuhara, Tokyo; Okihiko Sakamoto, Yokohama, all of (JP)

(73) Assignee: Shiseido Company, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/883,044

(22) Filed: Jun. 26, 1997

(30) Foreign Application Priority Data

Jun. 28, 1996 (JP) .............................................. 8-188578
Mar. 28, 1997 (JP) .............................................. 9-95297

(51) Int. Cl.⁷ .............................................. A61K 35/78
(52) U.S. Cl. ........................ 424/725; 424/744; 424/773
(58) Field of Search .............................. 424/195.1, 725, 424/744, 773; 514/884

(56) References Cited

U.S. PATENT DOCUMENTS

| | | | | |
|---|---|---|---|---|
| 4,540,571 A | * | 9/1985 | Schimanski | 424/94.1 |
| 4,885,157 A | * | 12/1989 | Fiaschetti | 424/59 |
| 4,959,214 A | * | 9/1990 | McAnalley | 424/195.1 |
| 5,356,811 A | | 10/1994 | Coats | 435/267 |

FOREIGN PATENT DOCUMENTS

| | | | |
|---|---|---|---|
| DE | 4130324 | * | 3/1993 |
| JP | 61254510 | * | 5/1985 |
| JP | 6-71413 | | 9/1994 |
| JP | 07274977 | * | 10/1995 |
| JP | 9-75026 | | 3/1997 |
| WO | WO 8501655 | * | 1/1985 |
| WO | 8501655 | * | 4/1985 |
| WO | 94/21786 | * | 9/1994 |
| WO | WO 9421786 | * | 9/1994 |

OTHER PUBLICATIONS

Harada et al., Agric. Biol. Chem., 48:2843–2845, abstract only, 1984.*
Lawless, The Illustrated Encyclopedia of Essential Oils, The Complete Guide to the Use of Oils in Aromatherapy and Herbalism, Barnes and Noble, Inc., 2nd printing, 1995, Element Books Ltd., 1st printing, Apr. 1992, p. 135.*
The Merck Index, Tenth Edition, Merck & Co., Inc., Rahway, NJ, p. 1312, entry #8996, 1983.*
Patent Abstracts of Japan, Publication No. 07274977, Publication Date Apr. 14, 1994, Application No. 6075199.

* cited by examiner

Primary Examiner—Christopher R. Tate
Assistant Examiner—Randall Winston
(74) Attorney, Agent, or Firm—Foley & Lardner

(57) ABSTRACT

An external skin treatment composition is described that comprises a "unicellularized" plant. This composition exhibits superior stability of the effective plant ingredients, superior moisture retention, and superior elimination of specific free radicals, and it offers sustained release of the effective plant ingredients. Methods are disclosed to unicellularize plants with, for example, an enzyme.

8 Claims, 10 Drawing Sheets

1: ALOENIN, 2: ISOBARBALOIN (ALOIN B),
3: BARBALOIN (ALOIN A), 4: FERULOYLALOESIN

EXTERNAL SKIN TREATMENT COMPOSITION

BACKGROUND OF THE INVENTION

1. Field of the Invention

The present invention relates to an external skin treatment composition containing a unicellularized plant. More specifically, it relates to an external skin treatment composition which enables the features of the plant which is unicellularized, including the features which remain just potential in an extract etc. of the plant, to be manifested to the maximum extent in an external skin treatment composition.

2. Description of the Related Art

The original objective of a cosmetic composition may be considered to have been to protect the body from nature. However, todays when science has made such progress, the objective has now become to keep the body clean, to use a makeup etc. to enable the human beings to express themselves beautifully and attractively and please themselves—an inborn human desire, and to protect the skin etc. from UV rays, drying, etc. to try to prevent aging, increase the number of years of beauty, and enjoy a pleasant life.

To achieve these objective's, various attempts have been made until now in the area of the development of cosmetic compositions.

For example, attempts have been made to involve formulating various types of chemical ingredients to impart the corresponding functions of those ingredients to the cosmetics or creating various types of preparations by ingeniously processing the basic ingredients. Various types of new cosmetics have been produced as a result.

There are many problems which remain to be solved despite these attempts. These are becoming major hurdles.

In particular, when trying to impart various functions to a single cosmetic composition, the types of the chemicals formulated inevitably become larger and, along with this, there are greater limitations due to prohibitions in formulations.

To solve these problems, various attempts are now under way.

SUMMARY OF THE INVENTION

Accordingly, the object of the present invention is to provide an external skin treatment composition such as a cosmetic composition which can solve the above problems inherent in, for example, contemporary cosmetic compositions to the maximum extent possible.

In accordance with the present invention, there is provided an external skin treatment composition comprising a unicellularized plant in a medium.

BRIEF DESCRIPTION OF THE DRAWINGS

The present invention will be better understood from the description set forth below with reference to the accompanying drawings, wherein.

DESCRIPTION OF THE PREFERRED EMBODIMENT

Figure 1:
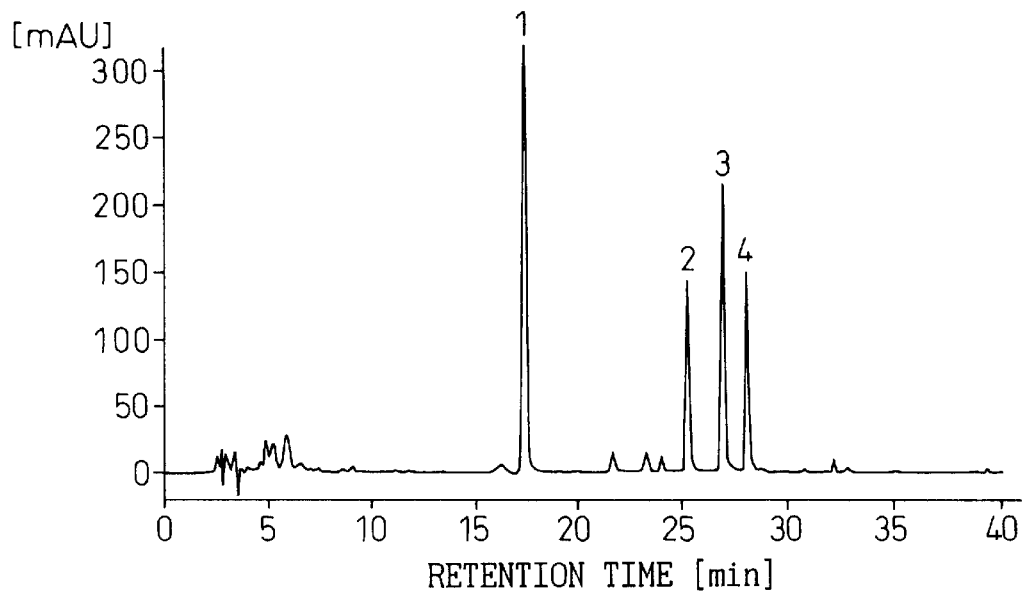
FIG. 1 is a chart of the results of high pressure liquid chromatography of phenol glycoside ingredients of unicellularized aloe.

The present inventors felt that it was necessary to find completely new ideas about ingredients so as to solve the above problems and conducted intensive studies toward that end. As a result, we found that by formulating a "unicellularized plant", that is, a plant which has been separated into its cellular units, as an effective ingredient in the cosmetic composition, they were able to manifest the features of the plant which is unicellularized, including the features which remain just potential in extracts etc. of the plant, to the maximum extent in a cosmetic composition (for example, being superior in the stability of the effective ingredients in the plant along with time, being superior in moisture retention-effect, being superior in effect of elimination of specific free radicals, and having the effect of a retained release of the effective ingredients in the plant), whereby the present invention was completed.

Further, the present invention provides an external skin treatment composition which makes use of the superior properties of chemicals of a unicellularized plant.

The "unicellularized plant" blended in the external skin treatment composition of the present invention means a plant, seaweed, or other natural material having cell walls which is processed by a means such as enzymatic decomposition or mechanical separation so as to selectively separate or destroy the intercellular substances without breaking down the cell walls and thereby break the material down into cellular units (single cells or cell masses) which are then made into a pultaceous state, liquid composition, or freeze-dried product.

Unicellularized plants are already being used in functional foods and so clearly have no problem in safety when blended into an external skin treatment composition.

The material of the unicellularized plant is not particularly limited so long as it is a plant having cell walls such as vegetables, fruits, seaweed, and medicinal herbs. The specific materials are suitably selected in accordance with the specific objective of the external skin treatment composition in which the unicellularized plant is to be blended.

These plant is first washed, sterilized, and otherwise preliminarily processed and then subjected to the unicellularization process.

As a typical method for this unicellularization process, the method of selectively breaking down the intercellular substances such as pectin by enzymatic treatment by pectinase etc. may be mentioned. Note that the unicellularized plant in the present invention assumes one which has cell walls. An enzyme for breaking down cell walls, that is, cellase, cannot be used as the means for the enzymatic treatment.

As the enzyme for unicellularization of the plant tissue used in the enzymatic treatment, polygalacturonase and pectinase derived from *Aspergillus niger,* Rhizopus sp., etc., pectin lyase derived from *Aspergillus niger, Aspergillus japonicus,* and other Aspergillus sp.; and pectolyase derived from *Aspergillus japonicus etc.* may be exemplified, but it is not particularly limited so long as it is able to selectively break down the intercellular substances of plants.

For the enzymes for unicellularization of plant tissue, it is possible to use one isolated by a usual, known method from enzyme material such as the above-mentioned Rhizopus sp. or Aspergillus sp.

When these plant tissue unicellularization enzymes are allowed to act on the material to be converted to a unicellular state, it is of course preferable that they be made to act at the optimal temperature of; the enzymes and under the optimal conditions of the optimal pH etc. and that the smallest amount be used.

Note that the optimal temperature for the above plant tissue unicellularization enzymes is generally 30 to 40° C. and the optimal pH is 4 to 5.

Further, after the enzymatic reaction, by removing the substances which tend to remain such as the epidermis (outer skin) of the plant, the fibrous matter, the core, the seeds, etc. by sieving using a sieve of for example 22 mesh size (pore size 710 $\mu$m), it is possible to,make a pultaceous unicellular suspension capable of formulating in the external skin treatment composition of the present invention.

Instead of the pultaceous unicellular suspension, it is possible to remove the water from the suspension by a method such as centrifugation (1500×g for at least 10 minutes) to obtain a unicellular paste or dried specimen which may then be blended with the external skin treatment composition of the present invention.

However, the pectin etc. constituting the intercellular substances have complicated, diverse structures. Neutral saccharides are included in the side chains and main chains. Further, it is believed there is bonding with hemicellulose. Separation as a unicellularized plant is therefore difficult by mechanical processes alone. However, it is possible to prepare the desired unicellular plant using a mechanical method in the case of leaves etc. of garden zinnia.

The amount of the unicellularized plant prepared in this way blended into the external skin treatment composition of the present invention is not particularly limited so long as it is determined by the type of the plant which is unicellularized, the effect desired from the formulating of the unicellularized plant, the form of the external skin treatment composition of the present invention, etc. So long as formulating in the state of the preparation is possible, it may be formulated in a range of at least 0.001% by weight and not more than 30% by weight of the external skin treatment composition. Generally, it is preferably formulated in a range of 0.1 to 10% by weight of the external skin treatment composition. More preferably it is formulated in a range of at least 1.0% by weight of the external skin treatment composition and not more than 8.0% by weight.

The external skin treatment composition of the present invention, comprises the unicellularized plant thus prepared formulated into an external skin treatment composition, can express the features of the plant which is unicellularized, including features which remain just potential in an extract of the plant etc., to the maximum extent in the external skin treatment composition.

For example, by formulating unicellularized carrot described in the later mentioned Examples into an external skin treatment composition, diverse superior effects are achieved such as superiority in the stability over time of the β-carotene and other effective ingredients of carrots, a superiority in moisture retention effect, a superiority in the effect of elimination of specific free radicals (hydroxy radicals (OH.)), and an effect of retained release of the above effective ingredients.

Further, by formulating unicellularized aloe in an external skin treatment composition, there are a superiority in moisture retention effect, a superiority of stability over time of the aloenin and other effective ingredients in aloe, and promotion of the proliferation of fibroblasts forming the epidermis of the skin. Further, there are various superior effects such as promotion of collagen-production.

Further, by formulating flower of the Freesia which has been unicellularized into an external skin treatment composition, there is the effect of elimination of specific free radicals (hydroxy radicals (OH.)) and various other effects such as a moisture retention effect and effect of stabilization of colors.

Further, by formulating the rhizome of an iris which has been unicellularized into an external skin treatment composition, there are various effects such as a moisture retention effect.

In the external skin treatment composition of the present invention, the type and form of the unicellularized plant which is formulated is not particularly limited so long as it can be formulated into the external skin treatment composition of the present invention physicochemically and the above effects can be exhibited in the external skin treatment composition of the present invention.

That is, as mentioned above, it is possible to formulate a unicellularized plant derived from a vegetable, fruit, seaweed, medicinal herb, etc. in an external skin treatment composition of the present invention. Unicellular plants of any form such as pultaceous unicellular suspensions, unicellular pastes, dried specimens, etc. may be formulated into the external skin treatment composition of the present invention. Further, one type of these unicellularized plants may be blended alone into the external skin treatment composition of the present invention or two or more types may be formulated in combination with each other.

Note that by just formulating the unicellularized plant as mentioned above, the-external skin treatment composition of the present invention can exhibit various superior effects. However, the formulating into the external skin treatment composition of the present invention of other chemical ingredients for the purpose of imparting effects which the external skin treatment composition would generally exhibit by the formulating of other chemical ingredients is possible to an extent where the formulating does not impair the desired effects of the present invention.

For example, when the external skin treatment composition of the present invention is used as a sun care product, it is possible to formulate, in the external skin treatment composition of the present invention, p-aminobenzoic acid and other benzoic acid type UV absorbants, methyl anthranilate and other anthranilic acid type UV absorbants, octyl salicylate, phenyl salicylate, homomethyl salicylate, and other salicylic acid type UV absorbants, isopropyl p-methoxycinnamate, octyl p-methoxycinnamate, 2-ethylhexyl p-methoxycinnamate, glyceryl di-p-methoxycinnamate mono-2-ethylhexanoate, [4-bis (trimethylsiloxy)methylsilyl-3-methylbutyl]-3,4,5-trimethoxycinnamic acid esters and other cinnamic acid type UV absorbants, 2,4-dihydroxybenzophenone, 2-hydroxy-4-methoxybenzophenone, 2-hydroxy-4-methoxybenzophenone-5-sulfonic acid, sodium 2-hydroxy-4-methoxybenzophenone-5-sulfonic acid, and other benzophenone type UV absorbants, urocanic acid, ethyl urocanate, 2-phenyl-5-methylbenzoxazole, 2-(2'-hydroxy-5'-methylphenyl)benzotriazole, 4-tert-butyl-4'-methoxybenzoylmethane, etc.

To impart a moisture retention effect to the external skin treatment composition of the present invention, it is possible to formulate a humectant such as polyethylene glycol, propylene glycol, dipropylene glycol, 1,3-butylene glycol, hexylene glycol, glycerine, diglycerine, xylitol, maltitol, maltose, D-mannitol, gluten, glucose, fructose, lactose, sodium chondroitin sulfate, sodium hyalonate, sodium adenosine phosphate, sodium lactate, gallates, pyrrolidone carbonates, glucosamine, cyclodextrin, etc.

As the chemical ingredient, it is possible to formulate, into the external skin treatment composition of the present invention, vitamin A oil, retinol, retinol palmitate, inositol, pyridoxine chlorate, benzyl nicotinate, nicotinamide, dl-α-tocopheryl nicotine, magnesium ascorbyl phosphate, vitamin $D_2$ (ergocalciferol), dlα-tocopherol, potassium dl-α-tocopherol-2-L-ascorbic diester, dl-α-tocopheryl acetate, pantothenic acid, biotin, and other vitamins, estradiol, ethynylestradiol and other hormones, alginin, asparagic acid, cystine, cysteine, methionine, serine, leucine, tryptophan, and other amino acids, allantoin, azulene, glycyrrhetinic acid, and other antipyretics, arbutin and other whiteners, zinc oxide, tannic-acid, and other astringents, L-menthol, camphor, and other fresheners or sulfur, lysozyme chloride, pyridoxine chlorate, γ-oryzanol, etc. Further, it is possible to formulate various types of extracts having various medicinal effects. That is, it is possible to blend into the external skin treatment composition of the present invention Houttuynia cordate extract, Phellon dendron amurense Rupr extract, melilot extract, white dead nettle extract, licorice root extract, herbaceous peony extract, soapwort extract, dishcloth gourd extract, cinchona extract, creeping saxifrage extract, Sophora angustifolia extract, candock extract, common fennel extract, primrose extract, rose extract, Rehmannia glutinosa extract, lemon extract, Lithospermum erythrorhizon extract, aloe extract, iris rhizome extract, eucalyptus extract, field horsetail extract, sage extract, thyme extract, tea extract, seaweed extract, cucumber extract, clove extract, raspberry extract, melissa extract, carrot extract, horse chestnut extract, peach extract, peach leaf extract, mulberry extract, cornflower extract, hamamelis extract, placenta extract, thymus extract, silk extract, etc.

Note that the medicinal ingredients capable of formulating into the external skin treatment composition of the present invention are not limited by the above-mentioned medicinal ingredients. Further, the above-mentioned medicinal ingredients may be formulated alone into the external skin treatment composition of the present invention or two or more types of the above medicinal ingredients may be combined and formulated suitably depending upon the objective.

Further, the above medicinal ingredients may not only be used in a free form, but may also be formulated into the external skin treatment composition of the present invention in the form of a salt of an acid or base when capable of forming a salt or in the form of an ester when having a carboxylic acid group.

The external skin treatment composition of the present invention may be broadly used in the form of a pharmaceutical, a quasi-drug (ointment, dentifrice, etc., and cosmetic (facial cleanser, emulsion, cream, gel, essence (beauty liquid), pack, mask, or other basic cosmetic; foundation, lipstick, or other makeup cosmetic; oral cosmetic, aromatic cosmetic, hair cosmetic, body cosmetic, etc.) The form capable of being taken by the external skin treatment composition of the present invention is not limited to these forms however.

Further, a wide range of preparations are possible such as aqueous solutions, other solutions, emulsions, powders, oils, gels, ointments, aerosols, water-oil systems, water-oil-powder systems, etc.

In the external skin treatment composition of the present invention, it is possible to formulate a wide range of the usual known basic ingredients depending upon the form and preparation desired to an extent not impairing the desired effect of the present invention.

That is, it is possible to formulate into the external skin treatment composition of the present invention linseed oil, tsubaki oil, macadamia nut oil, corn oil, mink oil, olive oil, avocado oil, sasanqua oil, castor oil, safflower oil, apricot oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, teaseed oil, evening primrose oil, eggyoke oil, neetsfoot oil, liver oil, triglycerine, glycerine trioctanate, glycerine triisopalmitate, and other liquid oils and fats; coconut oil, palm oil, palm kernel oil, and other liquid or solid oils and fats; cacao fat, beef tallow, sheep fat, hog fat, horse fat, hydrogenated oil, hydrogenated castor oil, Japanese wax, Shea butter, and other solid oils and fats; beeswax, candelilla wax, cotton wax, carnauba wax, bayberry wax, tree wax, spermaceti, montan wax, bran wax, lanolin, reduced lanolin, hard lanolin, kapok wax, sugarcane wax, jojoba wax, shellac wax, and other waxes.

Further, it is also possible to formulate into the external skin treatment composition of the present invention cetyl octanate and other octanic acid esters, glyceryl tri-2-ethylhexanoate, pentaerythritol tetra-2-ethylhexanoate, and other isooctanic acid esters; hexyl laurate and other lauric acid esters, isopropyl myristate, octyldodecyl myristate, and other myristic acid esters, octyl palmitate and other palmitic acid esters, isocetyl stearate and other stearic acid esters, isopropyl isostearate and other isostearic acid esters, octyl isopalmitate and other isopalmitic acid esters,. isodecyl oleate and other oleic acid esters, diisopropyl adipate and other adipic acid diesters, diethyl sebacate and other sebacic acid diesters, diisostearyl malate, and other ester oils; liquid paraffin, ozocerite, squalane, squalene, pristane, paraffin, isoparaffin, ceresin, vaseline, microcrystalline wax, and other hydrocarbon oils, etc.

Further, it is also possible to formulate into the external skin treatment composition of the present invention dimethyl polysiloxane, methylphenyl polysiloxane, methylhydrogen polysiloxane, and other chain like siloxanes, octamethylcyclotetrasiloxane, decamethylcyclopentasiloxane, dodecamethylcyclohexasiloxane, and other cyclic siloxanes, silicone resins having a three-dimensional network structures, silicone rubber, etc.

Further, it is also possible to formulate into the external skin treatment composition of the present invention soap base, sodium laurate, sodium palmitate, and other fatty acid soaps, sodium laurosulfate, potassium laurosulfate, and other higher alkyl sulfate ester salts, POE laurosulfate triethanol amine, sodium POE laurosulfate, and other alkyl ester sulfate ester salts, sodium lauroylsarcosine and other N-acylsarcosine acids, sodium N-myristyl-N-methyltaurine, sodium N-cocoyl-N-methyl taurate, sodium laurylmethyl taurate, and other higher fatty acid amide sulfonates, sodium POE oleyl ether phosphate, POE stearyl ether phosphate, and other phosphate ester salts, sodium di-2-ethylhexylsulfosuccinate, sodium monolauroylmonoethanol amide polyoxyethylene sulfosuccinate, sodium laurylpolypropylene glycol sulfosuccinate, and other sulfosuccinates, linear sodium dedecylbenzensulfonate, linear dodecylbenzensulfonate triethanol amine, linear dodecyl benzensulfate, and other alkylbenzensulfonates, sodium N-lauroylglutamate, disodium N-stearoylglutamate, monosodium N-myristoyl-L-glutamate, and other N-acylglutamates, sodium hydrogenated castor oil fatty acid glycine sulfate and other higher fatty acid ester sulfate ester salts, Turkey red oil and other sulfated oils, POE alkyl ether carboxylic acid, POE alkylaryl ether carboxylate, α-olefinsulfates, higher fatty acid ester sulfonates, secondary alcohol sulfate ester salts, higher fatty acid alkylolamide sulfate ester salts, sodium lauroyl monoethanolamide succinate, N-palmitoyl asparaginate ditriethanol amine, sodium caseine, and other anionic surfactants;

Stearyl trimethyl ammonium chloride, lauryl trimethyl ammonium chloride, and other alkyl trimethyl ammonium salts, distearyldimethyl ammonium chloride, dialkyldimethyl ammonium chloride salts, poly(N,N'-dimethyl-3,5-methylenepiperidinium)chloride, cetylpyridinium chloride and other alkyl pyridinium salts, alkyl quaternary ammonium salts, alkyl dimethylbenzyl ammonium salts, alkyl isoquinolinium salts, dialkyl morphonium salts, POE alkyl amines, alkyl amine salts, polyamine fatty acid derivatives, amyl alcohol fatty acid derivatives, benzalkonium chloride, benzethonium chloride, and other cationic surfactants; sodium 2-undecyl-N,N,N-(hydroxyethylcarboxymethyl)-2-imidazoline, 2-cocoyl-2-imidazoliniumhydroxide-1-carboxyethyloxy-2-sodium salt, and other imidazoline family bipolar surfactants, 2-heptadecyl-N-carboxymethyl-N-hydroxyethylimidazolinium betaine, lauryldimethyl-aminoacetate betaine, alkyl betaine, amide betaine, sulfo betaine, and other betaine family surfactants, and other bipolar surfactants;

Sorbitan monooleate, sorbitan monoisostearate, sorbitan monolaurate, sorbitan monopalmitate, sorbitan monostearate, sorbitan sesquioleate, sorbitan trioleate, diglyceryl sorbitan pentaoctanoate, diglyceryl sorbitan tetraoctanoate, and other sorbitan fatty acid esters, glycerin mono cotton seed oil fatty acid, glycerin monoerucate, glycerin sesquioleate, glycerin monostearate, glycerin α,α-oleate pyroglutamate, monostearate glycerin malic acid and other glycerin polyglycerin fatty acids, propylene glycol monostearate and other propylene glycol fatty acid esters, hydrogenated castor oil derivatives, glycerin alkyl ethers, polyoxyethylene methylpolysiloxane copolymers, and other lyophilic nonionic surfactants;

POE sorbitan monooleate, PO-sorbitan monostearate, POE-sorbitan monooleate, POE-sorbitan tetraoleate, and other POE sorbitan fatty acid esters, POE-sorbite monolaurate, POE-sorbitan monooleate, POE-sorbite pentaoleate, POE-sorbitan monostearate, and other POE sorbitan fatty acid esters, POE-glycerin monostearate, POE-glycerin monoisostearate, POE-glycerin triisostearate, and other POE glycerin fatty acid esters, POE monooleate, POE distearate, POE monodioleate, distearate ethylene glycol, and other POE fatty acid esters, POE lauryl ethers, POE oleyl ethers, POE stearyl ethers, POE behenyl ethers, POE2-octyldodecyl ethers, POE cholestanol ethers, and other POE alkyl ethers, POE octyl phenyl ethers, POE nonyl phenyl ethers, POE dinonyl phenyl ethers, and other POE alkyl phenyl ethers, Pluronic and other pluaronics, POE.POP cetyl ethers, POE.POP-2-decyltetradecyl ethers, POE.POP monobutyl ethers, POE.POP hydrated lanolin, POE.POP glycerin ethers, and other POE-POP alkyl ethers, Tetronic and other tetra-POE.tetra-POP ethylene diamine condensation products, POE castor oil, POE hydrogenated castor oil, POE hydrogenated castor oil monoisostearate, POE hydrogenated castor oil triisostearate, POE hydrogenated castor oil monopyroglutamate monoisostearate diester, POE hydrogenated castor oil maleic acid and other POE castor oil hydrogenated castor oil derivatives, POE sorbitan beeswax and other POE beeswax lanolin derivatives, coconut oil fatty acid diethanolamide, laurate monoethanolamide, fatty acid isopropanolamide, and other alkanolamides, POE propylene glycol fatty acid esters, POE alkylamines, POE fatty acid amides, sucrose fatty acid esters, POE nonylphenyl formaldehyde condensation products, alkylethoxydimethylamineoxide, trioleylphosphoric acid, and other hydrophilic nonionic surfactants and other surfactants.

Further, it is also possible to formulate into the external skin treatment composition of the present invention methanol, ethanol, propanol, isopropanol, and other lower alcohols; cholesterols, cytosterols, phytosterols, lanosterols, and other sterols, etc.

Further, it is also possible to formulate into the external skin treatment composition of the present invention arabia gum, tragacanth, galactan, carob gum, guar gum, karaya gum, carragheenin, pectin, agar, quince seed, algae colloids (algae extract), starch (rice, corn, potato, wheat), and other plant type polymers, dextran, succinoglucan, pulleran, and other microbial type polymers, carboxymethyl starch, methylhydroxypropyl starch, and other starch type polymers, collagen, casein, albumin, gelatin, and other animal type polymers, methyl cellulose, nitrocellulose, ethyl cellulose, methylhydroxypropyl cellulose, hydroxyethyl cellulose, sodium cellulose sulfate, hydroxypropyl cellulose, sodium carboxymethyl cellulose, crystalline cellulose, cellulose powder, and other cellulose type polymers, sodium alginate, alginic acid propylene glycol esters and other alginic acid type polymers, polyvinylmethyl ethers, carboxyvinyl polymers (CARBOPOL etc.), and other vinyl type polymers, polyoxyethylene type polymers, polyoxyethylene-polyoxypropylene copolymer type polymers, sodium polyacrylate, polyethylacrylate, polyacerylamide, and other acryl type polymers, polyethyleneimine, cation polymers, bentonite, aluminum magnesium silicate, laponite, hectonite, anhydrous silicic acid, and other inorganic type water-soluble polymers, etc.

Further, it is also possible to formulate into the external skin treatment composition of the present invention alanine, sodium edetate, sodium polyphosphate, sodium metaphosphate, phosphoric acid, and other metal ion sealants; 2-amino-2-methyl-1-propanol, 2-amino-2-methyl-1,3-propanediol, potassium hydroxide, sodium hydroxide, L-alginin, L-lysin, triethanolamine, sodium carbonate, and other neutralizing agents; lactic acid, citric acid, glycolic acid, succinic acid, tartaric acid, dl-malic acid, potassium carbonate, sodium hydrogencarbonate, ammonium hydrogencarbonate, and other pH adjusters; ascorbic acid, α-tocopherol, dibutylhydroxytoluene butylhydroxyanisole, and other antioxidants.

Further, it is also possible to formulate into the external skin treatment composition of the present invention benzoic acid, salicylic acid, carbolic acid, sorbic acid, p-oxybenzoic acid esters, p-chlorometacresol, hexachlorophene, benzalkonium chloride, chlorohexidine chloride, trichlorocarbanilide, photosensitive element, phenoxyethanol, and other antibacterials.

Further, it is also possible to formulate into the external skin treatment composition of the present invention, if necessary, a suitable perfume, color, etc. to an extent not impairing the desired effect of the present invention.

Here, the above basic ingredients were all examples. The basic ingredients which may be formulated into the external skin treatment composition of the present invention are not limited by these basic ingredients.

These basic ingredients may be formulated into the external skin treatment composition of the present invention in suitable combination based upon the formulations based on the desired form.

Specific formulations of the external skin treatment composition of the present invention will be described in the following Examples.

EXAMPLES

The present invention will now be further explained in detail by, but is not limited to, the following Examples.

Reference Example A

Preparation of Unicellularized Carrot
(1) Preparation of Plant Tissue Unicellularizing Enzyme 1 kg of sawdust was mixed with 6 kg of wheat seed coats. 5 liters of tap water containing 30 ml of 1% HCl was sprinkled on this, then the ingredients were mixed. The mixture was steam sterilized at 100° C. for 1 hour then commercially available Rhizopus spores were sprinkled on it at 34–35° C. This was incubated at 30° C. and a relative humidity (RH) of 85% for 48–50 hours and then dried and used as the malt.

Hot water was added at a ratio of 3 parts by weight based on 1 part by weight of the malt. The extracted filtrate was cooled to 0° C., then acetone similarly cooled to 0° C. was added to this. The 40 to 60% saturated precipitated fraction was collected by centrifugation, then was dried and used as the plant tissue unicellularizing enzyme.

(2) Preparation of Unicellularized Carrot 8 kg of carrots immersed for 10 minutes in sodium hypochlorite for sterilization and washing was minced into 3 mm squares by a food slicer. 2 kg of sterilized cold water was added to this, the pH was adjusted to 4.3 by 20% citric acid solution, then steam was blown in to sterilize the mixture at above 90° C. for about 10 minutes.

The enzyme solution prepared in the above (1) was added in an amount of 0.5% by weight to the carrots, then a mixer was used under a sterilizing process to mix this at a high speed for 1 hour (water temperature of outer jacket 40° C.) to macerate it.

After the end of the maceration, the nondecomposed fibrous matter was removed by a 20 mesh stainless-steel sieve to obtain 9.5 kg of a pultaceous unicellularized carrot suspension.

This pultaceous unicellularized carrot suspension was processed by a freeze-drying machine (made by FTS) to prepare a freeze-dried powder of the pultaceous unicellularized carrot.

Note that the above Rhizopus fungi scolecospore has been allowed to be used in food, and therefore, is extremely safe. The fact that the enzyme derived from this Rhizopus fungi scolecospore is mixed in the above unicellularized carrot does not pose any problem in respect to safety at all. Further, when the extracellular protein of carrots is an issue, the above unicellularized carrot is centrifuged (about 3000 rpm) and the supernatent obtained is replaced with water so as to remove the extracellular protein from the system.

Reference Example B

Preparation of Unicellularized Aloe
(1) Preparation of Unicellularized Aloe 10 kg of finely cut aloe (i.e., Aloe arborescens) was minced by a food slicer etc. An enzyme aqueous solution (Macelozyme (phonetic) R-200 (made by Yakult Yakuhin Kogyo) dissolved in an amount of 0.04% by weight with respect to the minced aloe in a volume of water of 50% of the volume of the minced aloe) was added to the minced aloe and the mixture was stirred at 40° C. for 6 hours (75 rpm).

After the end of the stirring, the reaction product was passed through a 710 μm mesh sieve, then treated at 85° C. for 30 minutes to deactivate the enzyme.

After this enzyme deactivation treatment, a 300 μm size mesh sieve was used to filter the enzyme deactivated product. A suitable preservative was added to this to obtain the desired unicellularized aloe.

(2) Analysis by HPLC of Phenol Glycoside Ingredients of Unicellularized Aloe

What kind of structure the aloenin and other glycoside ingredients known as the main effective ingredients of aloe had in the unicellularized aloe was analyzed by high pressure liquid chromatography (HPLC).

Note that 100 mg of the freeze-dried powder of the unicellularized aloe obtained in the above (1) was extracted by methanol, the extract was agitated cold for 10 minutes by ultrasonic waves, then centrifuged at 3000 rpm for 15 minutes, then the supernatent obtained was used as the HPLC sample (10 μl).

HPLC Conditions

Column: CAPCELLPAK C18 (4.6 mmφ×250 mm: made by Shiseido Co., Ltd.)

Column temperature: 45° C.

Eluent: $CH_3CN(A)$—$H_2O(B)$ 0 minutes (12%(A)), 19 minutes (23%), 24 minutes (28%), 39 minutes (46%), 49 minutes (100%)

Elution rate: 1 ml/min

Detected wavelength: UV290 nm

A chart of the results of this HPLC analysis is shown in FIG. 1.

From FIG. 1, it is clear that the unicellularized aloe contains the ingredients generally considered the effective ingredients of aloe, that is, aloenin, isobarbaloin, barbaloin, and feruloylaloesin).

Reference Example C

Preparation of Unicellularized Freesia 500 g of only the flower portion of Freesia was collected and minced by a razor, then to 2 g thereof, 100 ml of an enzyme aqueous solution (Macelozyme (phonetic) R-200

(made by Yakult Yakuhin Kogyo) dissolved in an amount of 0.04 wt % with respect to the minced Freesia flower in a volume of water of 50% of the volume of the Freesia flower) was added. The mixture was stirred at 40° C. for 3 hours. After the end of the reaction, the enzyme treated product was filtered by a 710 μm mesh sieve to remove the residue to obtain the unicellularized Freesia flower.

Reference Example D

Preparation of Unicellularized Iris Rhizome 61.54 g of the portion of the rhizome of a peeled iris (*Iris parida*, Iridaceae) was minced. The above Macelozyme (phonetic) R-200 (0.08%; 49.2 mg) was dissolved in a volume of purified water (62 ml) equal to the plant and added. The mixture was stirred at 40° C. for 3 hours. After the end of the reaction, the mixture was filtered by a 710 μm mesh sieve and the residue removed to obtain the unicellularized iris rhizome.

Reference Example E

Preparation of Unicellularized Panax Ginseng 52.5 g of Panax ginseng (Araliaceae) was minced. The above Macelozyme(phonetic) R-200 (0.08%; 42.0 mg) was dissolved in a volume of purified water (106 ml) double of that of the plant and added. The mixture was stirred at 40° C. for 5.5 hours. After the end of the reaction, the mixture was filtered by a 710 μm mesh sieve and the residue removed to obtain the unicellularized Panax ginseng.

Reference Example F

Preparation of Unicellularized Citrus Unshiu 53.22 g of the peel of *Citrus unshiu* (Rutaceae) was minced. The above Macelozyme (phonetic) R-200 (0.08%; 43.0 mg) was dissolved in a volume of purified water (53 ml) equal to the plant and added. The mixture was stirred at 40° C. for 4.5 hours. Note that five minutes after the start of the reaction, an equal amount of purified water (53 ml) was added to the system. After the end of the reaction, the mixture was filtered by a 710 μm mesh sieve and the residue removed to obtain the unicellularized Citrus unshiu.

Reference Example G

Preparation of Unicellularized Sweety 79.90 g of the peel of Sweety was minced. The above Macelozyme (phonetic) R-200 (0.08%; 64.0 mg) was dissolved in a volume of purified water (80 ml) equal to the plant and added. The mixture was stirred at 40° C. for 4.5 hours. Note that five minutes after the start of the reaction, an equal amount of purified water (80 ml) was added to the system. After the end of the reaction, the mixture was filtered by a 710 μm mesh sieve and the residue removed to obtain the unicellularized Sweety.

Test Example A1

Figure 2:
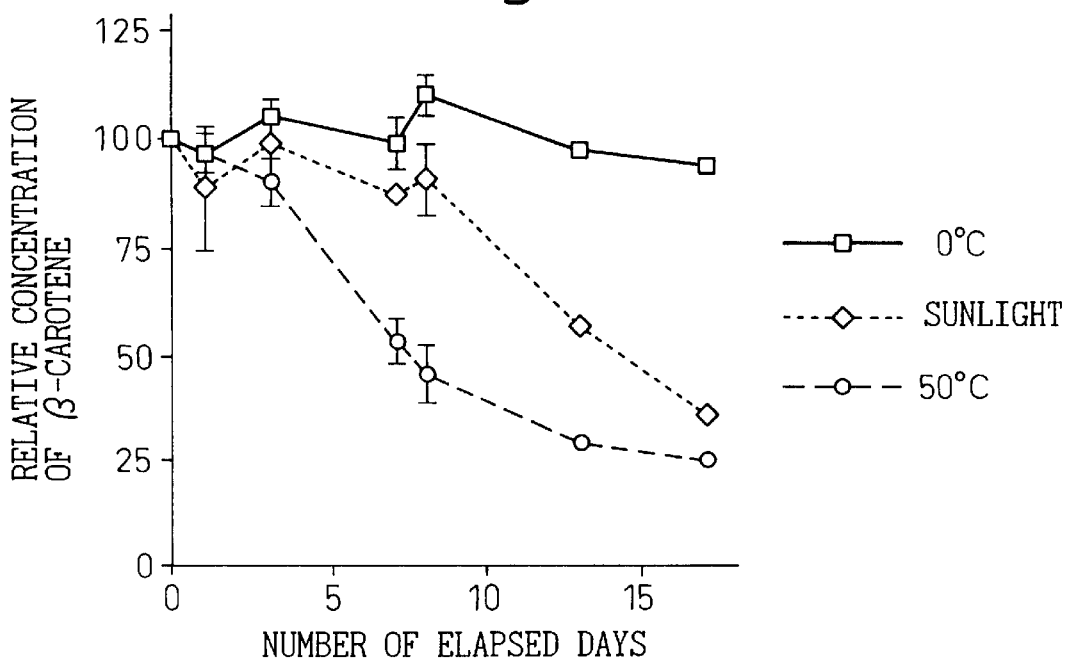
FIG. 2 is a view of the results of studies of the relative concentration of $\beta$-carotene in dried unicellularized carrot over time under various conditions.

Test of Stability of Unicellularized Carrot (1) The stability of the freeze-dried powder of the pultaceous unicellularized carrot prepared in the above Reference Example A was studied at relative concentrations of the β-carotene (FIG. 2).

FIG. 2 is a graph of the results of a study over time of the relative concentrations of β-carotene at □: 0° C. (dark place), ◊: sunlight (room temperature), and ○: 50° C. (dark place).

Figure 3:
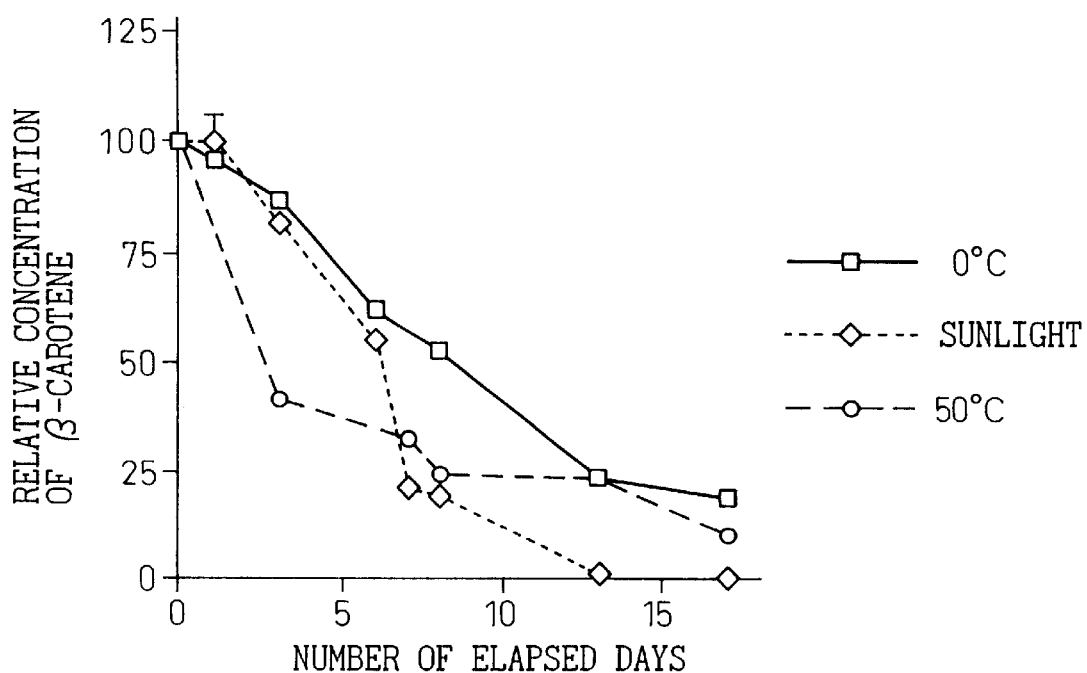
FIG. 3 is a view of the results of a study of the stability of $\beta$-carotene of a dried product of an extract of carrot under various conditions.

As opposed to this, FIG. 3 is a graph of the results of a study of the stability of β-carotene under the same conditions as with the test of the dried product of the extract of carrot (carrot extracted three times by acetone and then dried under vacuum).

From FIG. 2 and FIG. 3, it is found that the β-carotene of unicellularized carrot at 0° C. and under sunlight was extremely superior in stability over time compared with the β-carotene of the carrot extract.

Note that the concentration of β-carotene was analyzed by high pressure liquid chromatography (ODS column (Capcelpak C18: made by Shiseido Co., Ltd.) That is, the β-carotene was eluted from the column by 100% acetonitrile and detected at 450 nm. The flow rate of the column was 2 ml/min.

(2) The stability of the pultaceous unicellularized carrot prepared in the above reference examples was studied.

Figure 4:
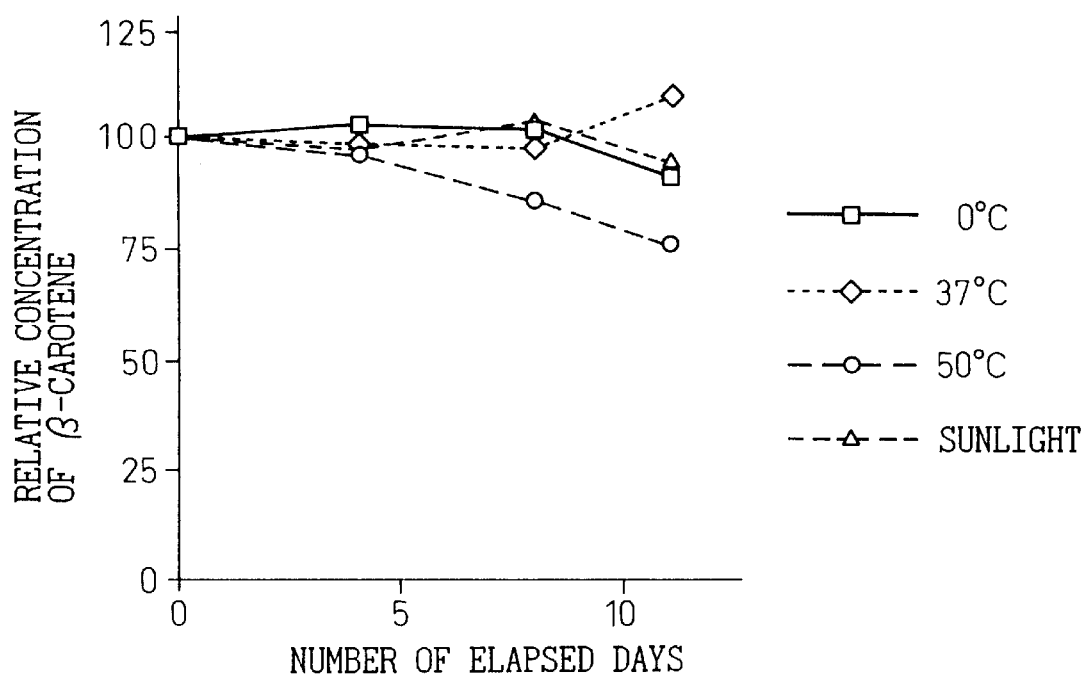
FIG. 4 is a view of the results of a study of the relative concentration of $\beta$-carotene of pultaceous unicellularized carrot under various conditions over time.

FIG. 4 is a graph of the results of a study over time of the relative concentrations of β-carotene of :.the above pultaceous unicellularized carrot at □: 0° C. (dark place):, ◊: 37° C. (dark place), ○: 50° C. (dark place), Δ: sunlight.

From FIG. 4, it is clear that the pultaceous unicellularized carrot is superior in stability of β-carotene over a dried product under any conditions.

That is, the superior stability of a unicellularized plant in an external skin treatment composition of the present invention, where the unicellularized plant is often brought into contact with water as a blending ingredient, is strongly suggested.

Test Example A2

Study of Moisture Retention Effect of Unicellularized Carrot

The moisture retention effect of unicellularized carrot (8 wt % aqueous solution) was studied in comparison with water, glycerin (8 wt % aqueous solution), a methanol extract of carrot (8 wt % aqueous solution), and DPG (dipropylene glycol) (8 wt % aqueous solution).

That is, 50 μl each of the above samples was placed on a chemical balance placed in a room held to 22° C. and a dry humidity of 45%. The change in weight was measured every three minutes for seven times in total. From the results, the coefficient of the rate of moisture evaporation in the sample (coefficient k of rate of moisture evaporation found as dW/dt=kW where the amount of moisture is W and the elapsed time is t, that is, logW=kt+C (C is a constant)) was calculated.

Figure 5:
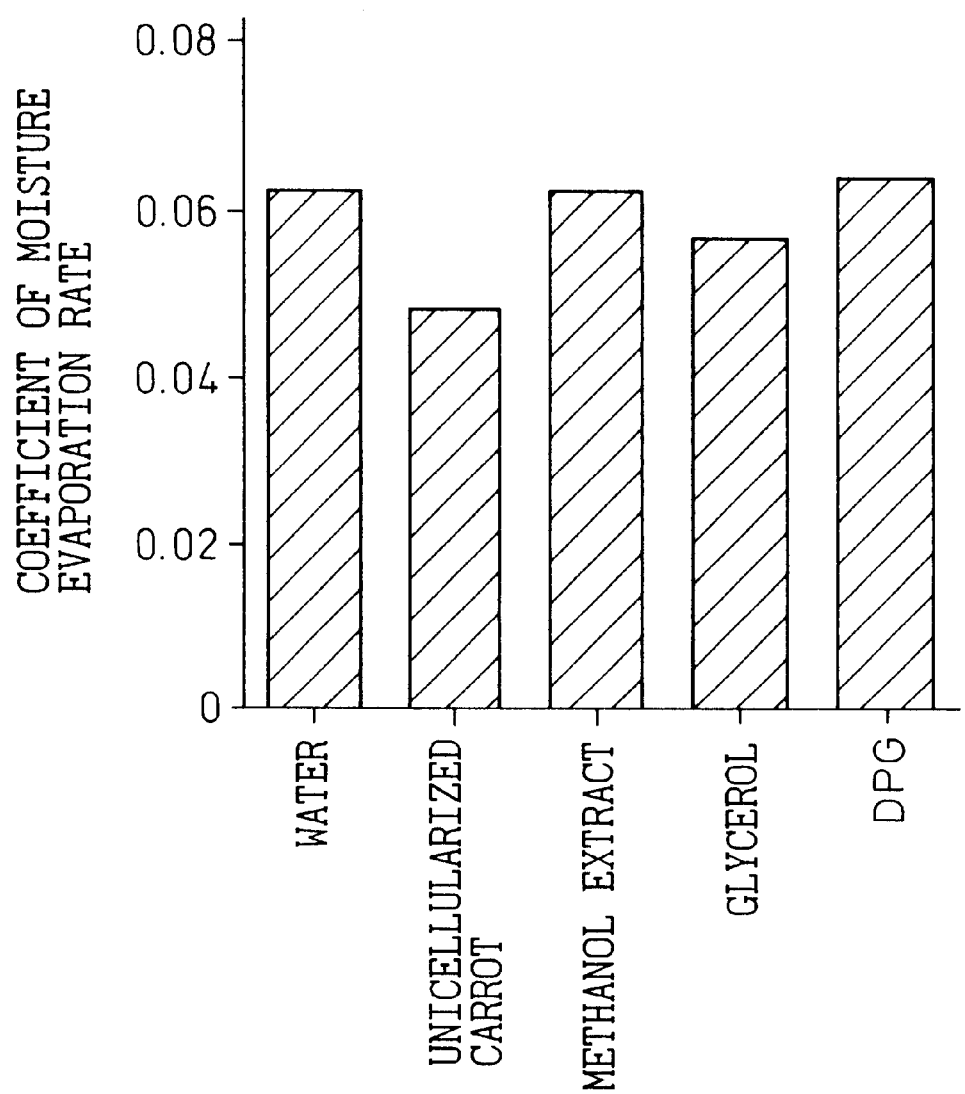
FIG. 5 is a view of a study of the moisture retention effect of unicellularized carrot.

FIG. 5 shows the results.

From the results, it is clear that the unicellularized carrot plant is more resistant to evaporation of moisture than not only water but also glycerin and dipropylene glycol, which are known as humectants, and the moisture retention effect is not observed in methanol extracts of carrot and is an effect based on the presence of the carrot as a unicellularized plant.

Test Example A3

Study of Slow Release of β-Carotene in Unicellularized Carrot

Figure 6:
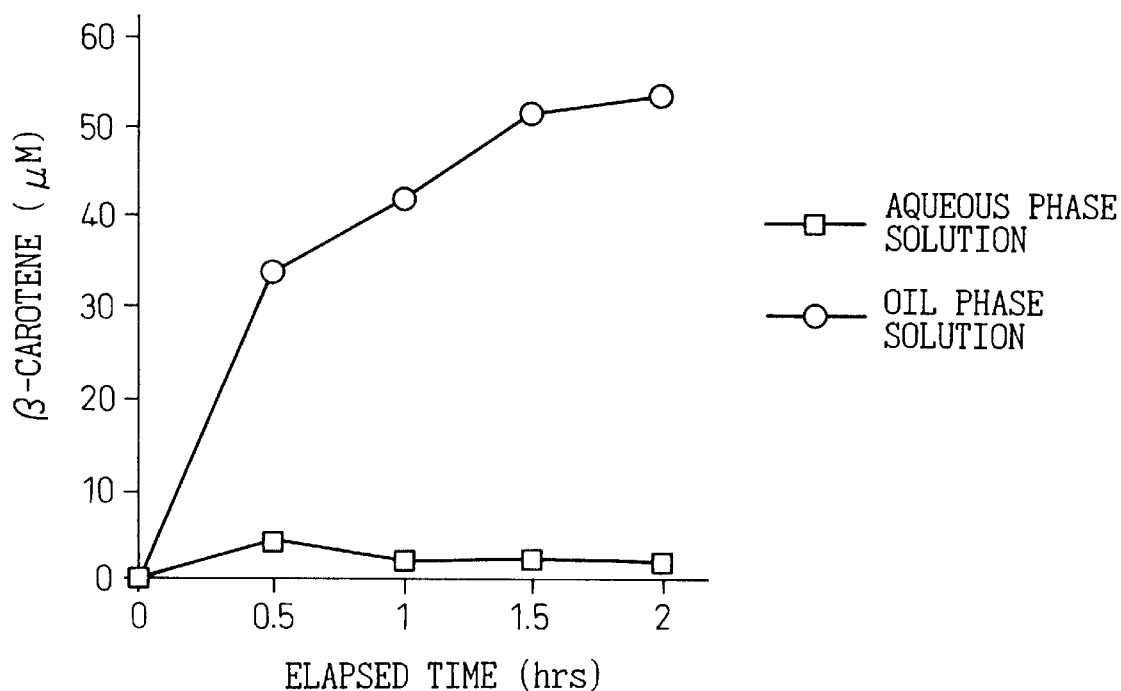
FIG. 6 is a view of a study of the slow release of $\beta$-carotene in unicellularized carrot.

The slow release of β-carotene with an aqueous phase solution containing the dried product of the unicellularized carrot prepared in Reference Example A added to an aqueous component containing ion exchanged water (81.2 parts by weight), dipropylene glycol (7.0 parts by weight), and brucine modified alcohol (5.0 parts by weight) to give a concentration of 30% by weight and with an oil phase-solution containing the same added to an oil component (glyceryl tri-2-ethylhexanoate) to give a concentration of 30% by weight was studied (FIG. 6).

That is, the above samples were incubated at 37° C., the extracellular solution was sampled over time, and the amount of β-carotene was analyzed by the method described in the above Test Example 1(1).

In FIG. 6, the aqueous phase solution (□) clearly did not release the β-carotene as easily as the oil phase solution (○).

From the results of FIG. 6, it is clear that the effective ingredients in the unicellularized plant are not released much at all to the outside of the unicellularized plant at the time of use when present in an aqueous phase, for example, when using the external skin treatment composition of the present invention as a cosmetic, but enable the provision of an external skin treatment composition of the present invention having a slow release effect of allowing a large amount of the effective ingredients to leach out after the elapse of a certain amount of time when the moisture evaporates and the oil part of the external skin treatment composition and the oily components on the skin come into contact with the unicellularized plant, for example, when the external skin treatment composition of the present invention is used.

This slow release effect is extremely useful in that it enables a substance which has superior properties such as a strong antioxidation action, but which is unstable outside the cells, such as β-carotene, to be blended as an ingredient of an external skin treatment composition while maintaining its inherent functions.

Test Example A4

Figure 7:
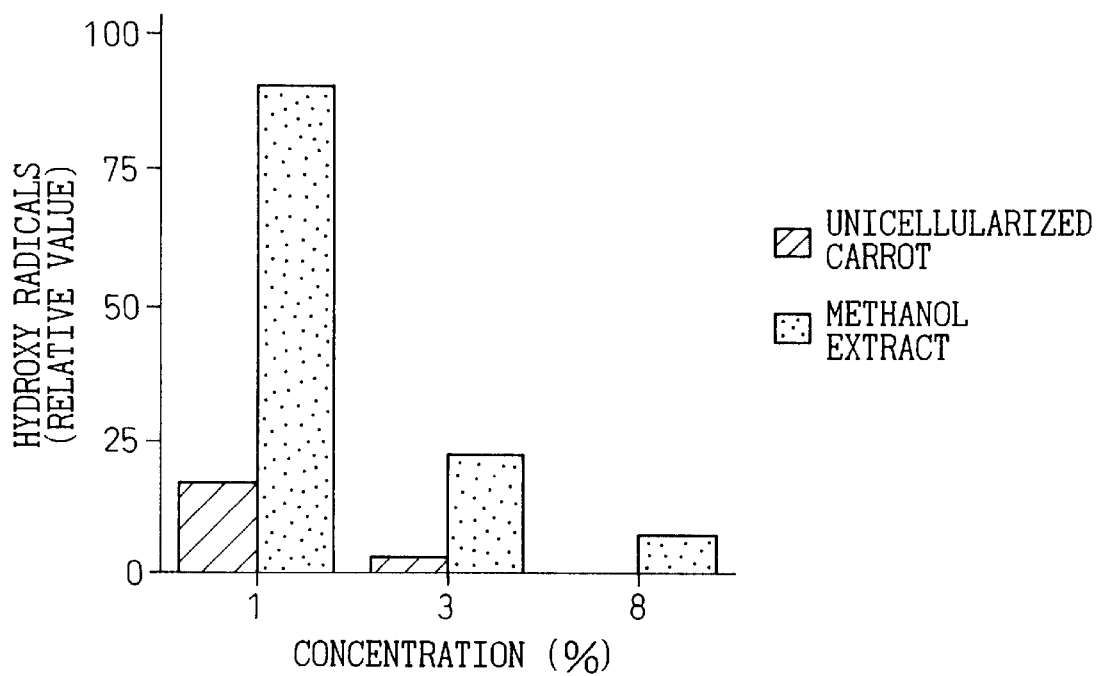
FIG. 7 is a view of a study of the effect of elimination of hydroxy radicals (OH.) in unicellularized carrot.

Study of Effect of Elimination of Hydroxy Radicals (OH.) in Unicellularized Carrot A study was made of the OH. elimination effect of the unicellularized carrot suspension prepared in Reference Example A and a methanol extract of carrot (FIG. 7).

That is, OH. was generated by hydrogen peroxide ($H_2O_2$) and $Fe^{2+}$ the OH. measured by the ESR spin trapping method.

Specifically, 50 µl of a 1 mM $FeSO_4$ aqueous solution and 20 µl of a 10% aqueous solution of dimethylpyrolin-N-oxide were added to 75 µl of a 10 mg/liter sample. To this, 75 µl of hydrogen peroxide (1 mM) was added and the mixture stirred for 30 seconds. After 75 seconds, the ESR spectrum was measured and the amount of the hydroxy radicals (OH.) compared by the height of the initial peaks.

From FIG. 7, it is clear that even compared with a methanol extract of carrot containing in large amounts β-carotene with its OH. eliminating effect, unicellularized carrot has a surprising OH. elimination effect in just a small concentration of 1% by weight.

OH. has the strongest reactivity among the active enzyme groups and, for example, causes protein modification or DNA cleavage. Therefore, if it were possible to suppress the generation of OH., it would be possible to control the aging of the skin and possible to maintain the skin healthier, but from the above results it is clear that by using a unicellularized plant as the ingredient for elimination of OH. in the external skin treatment composition, it is possible to impart to the external skin treatment composition a superior effect of control of aging.

Test Example B1

Figure 8:
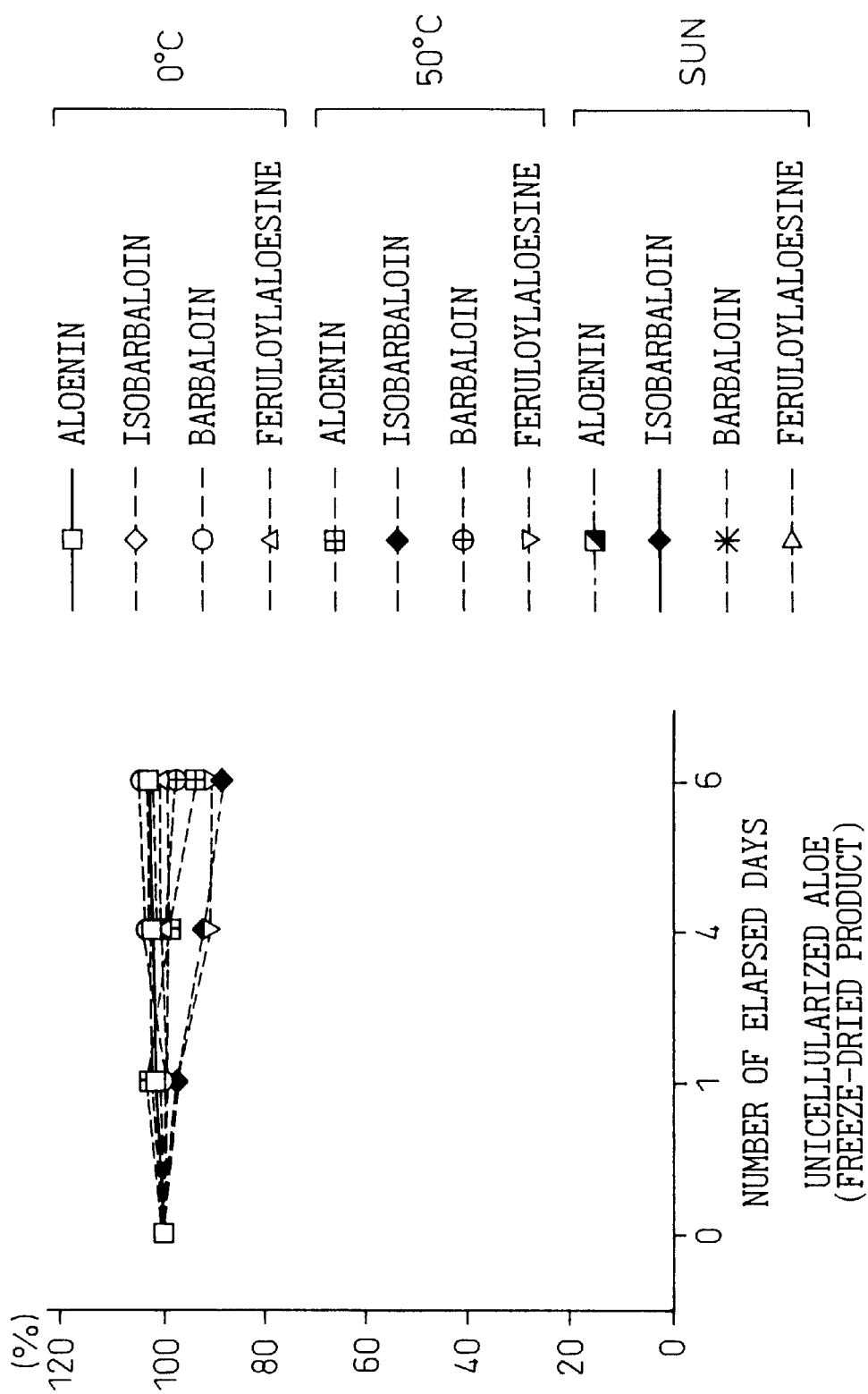
FIG. 8 is a view of a study of the stability of the effective ingredients included in aloe in unicellularized aloe along with time.

Test of Stability of Unicellularized Aloe (1) The stability of freeze dried powder of unicellularized aloe prepared in the above Reference Example B was studied at relative concentrations of the effective ingredients of aloe at the time of the start of the experiments (FIG. 8).

FIG. 8 is a graph of the results of a study over time of the relative concentration of the effective ingredients in unicellularized aloe specified by the above HPLC under the conditions shown at the right side of the figure (0° C.:0° C., blocked from light; 50° C.:50° C., blocked from light; SUN:under sunlight).

Figure 9:
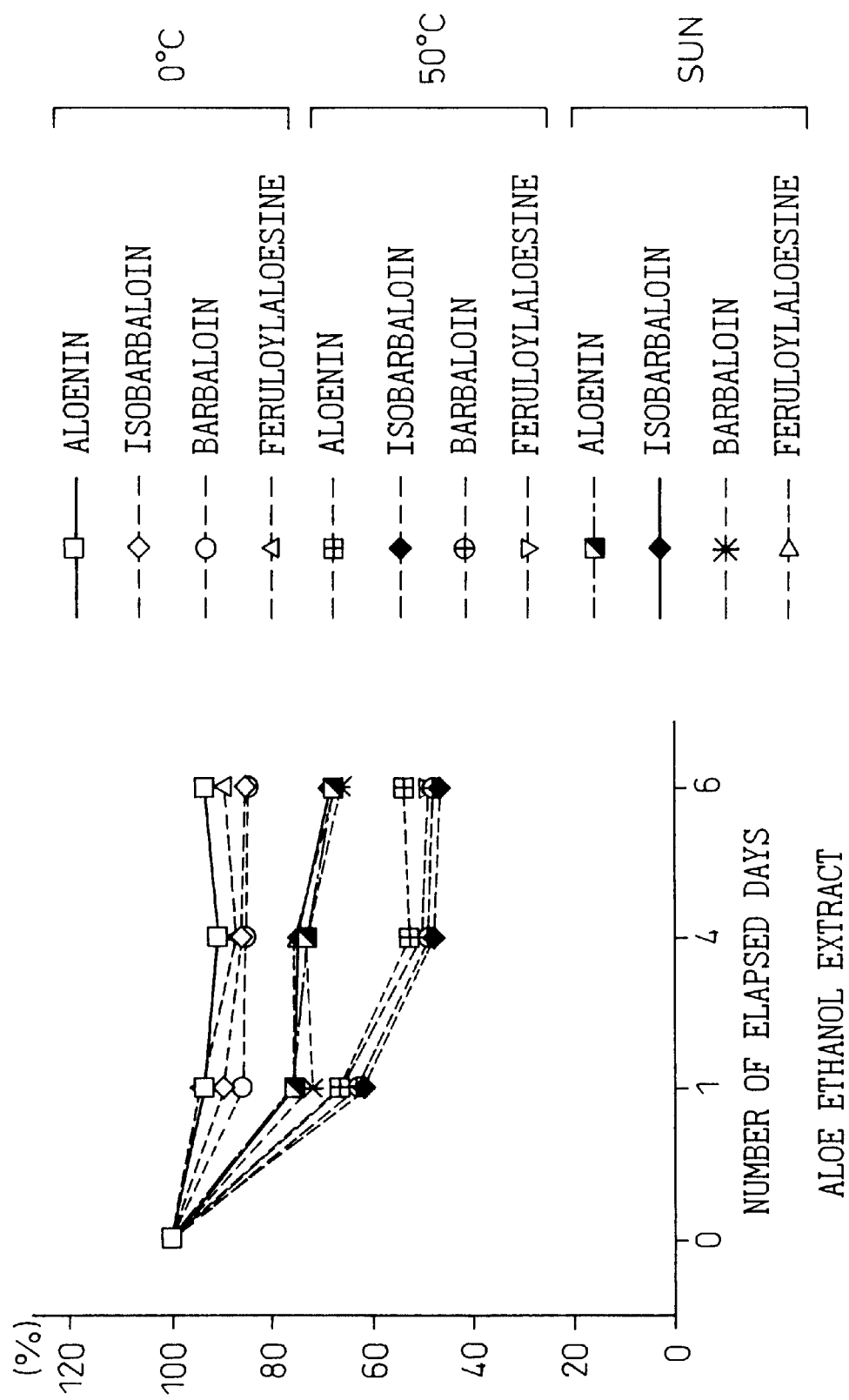
FIG. 9 is a view of a study of the stability of the effective ingredients included in aloe in an ethanol extract of aloe along with time.

As opposed to this, FIG. 9 is a graph of the results of a study of the stabilities of the effective ingredients observed in the above unicellularized aloe under the same conditions as with the test on the dried product of the aloe extract (aloe extracted three times by ethanol, then dried under vacuum).

From FIG. 8 and FIG. 9, it is seen that at 0° C., all of the tested ingredients for both the unicellularized aloe and the aloe extract were stable over time, but undersunlight and at 50° C., the tested ingredients in the aloe extract changed considerably over time. With the unicellularized aloe, however the tested ingredients all remained stable over time under all conditions.

From this, it is clear that there is an effective action of stabilization of effective ingredients over time in aloe which has been unicellularized.

Note that the concentration of the effective ingredients was analyzed by HPLC in the same way as the above Reference Example B (same conditions set).

Test Example B2

Study of Moisture Retention Effect of Unicellularized Aloe

The moisture retention effect of unicellularized aloe (5 wt % aqueous solution) was studied in comparison with water and an ethanol extract of aloe (5 wt % aqueous solution).

Note that the method of study of this moisture retention effect was the same as the method used in the above Test Example A2.

Figure 10:
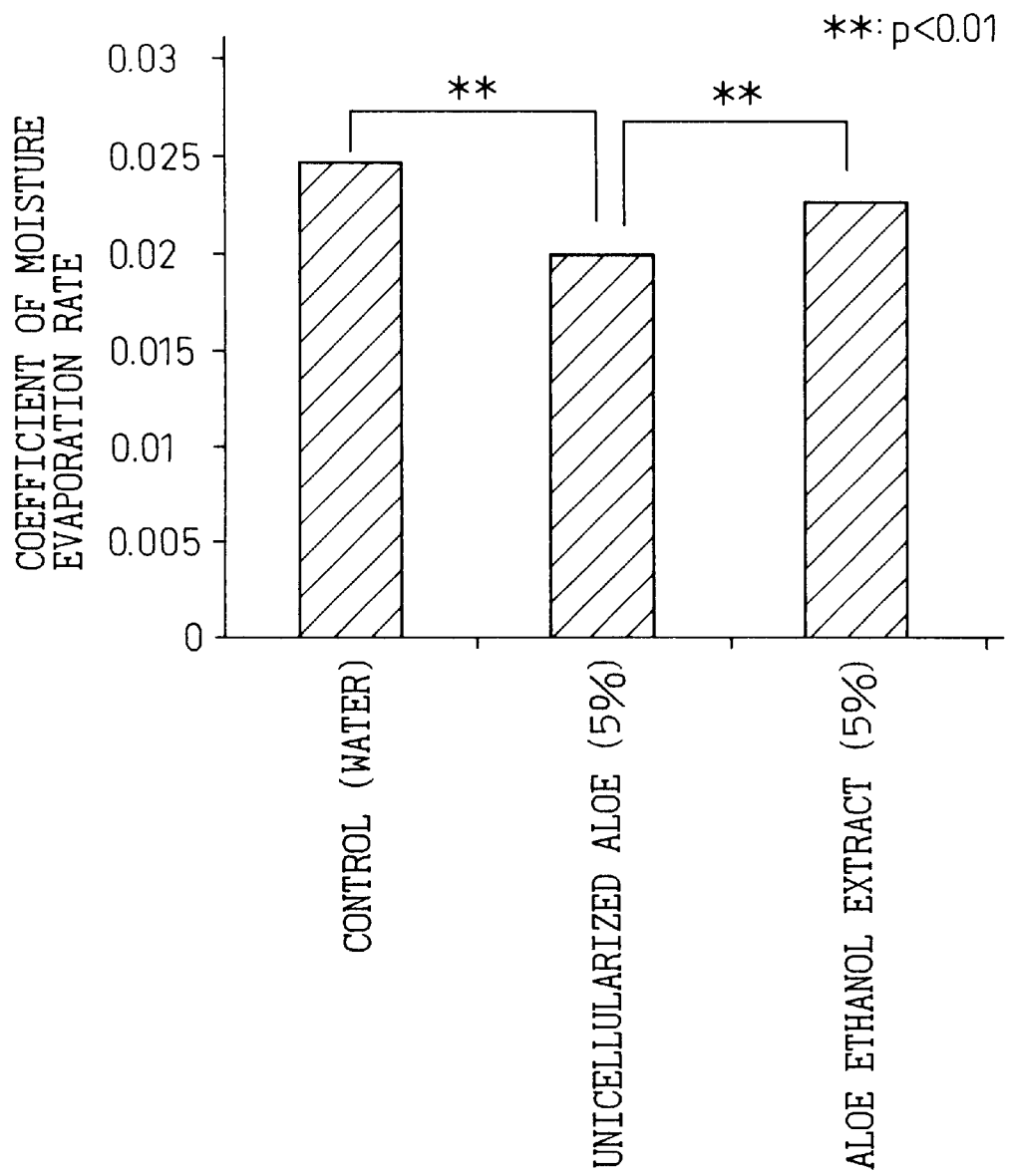
FIG. 10 is a view of a study of the moisture retention effect of unicellularized aloe.

FIG. 10 shows the results of the test.

From these results, it is clear that an extract of aloe does not show almost any moisture retention effect at all in relation to water, but unicellularized aloe clearly shows a significant moisture retention effect in relation to these. Further, from these results, it is clear that like with the case of the above Test Example A2, the moisture retention effect is an effect based on the presence of aloe as a unicellularized plant.

Test Example B3

Study of Effect of Proliferation of Human Skin Fibroblast by Unicellularized Aloe A certain number of human skin fibroblasts were sown in a 96 well plate for cell culture and incubated for 48 hours by Delbecco Modified Eagle Medium (DMEM) containing 10% fetal bovine serum (FBS), then the medium was replaced with DMEM medium containing 0.5%. FBS. To this, unicellularized aloe not containing a preservative (2.0 wt % aqueous solution) or an ethanol extract of aloe (2.0 wt % aqueous solution) was added and the mixture was incubated for 48 hours. After the end of the incubation, the amount of DNA in a well was measured by the method using "Hoechest 33258", a fluorescent substance which specifically bonds with thymidine (C. Labarca, K. Paigen, Analytical Biochemistry, 102; 344 to 352 (1980)) and the result made an indicator of the cell count.

Figure 11:
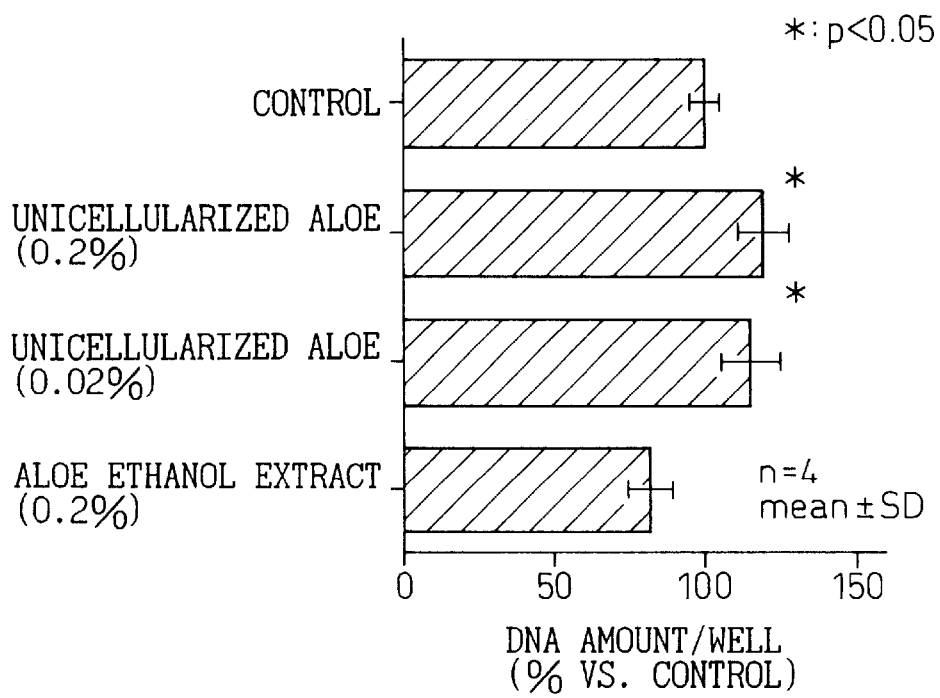
FIG. 11 is a view of a study of a proliferation effect of unicellularized aloe on human skin fibroblasts.

The results of the test are shown in FIG. 11. Note that in FIG. 11 the horizontal axis shows the relative value of the amount of DNA per well with respect to a control.

From FIG. 11, it is seen that the ethanol extract did not exhibit any effect of proliferation of the fibroblasts, while with the unicellularized aloe, a clear effect of proliferation of the fibroblasts was observed.

Test Example B4

Study of Effect of Promotion of Production of Collagen by Unicellularized Aloe In the same way as the above Test Example B3, a certain number of human skin fibroblast cells were sown in a 96 well plate for cell culture and incubated for 48 hours by Delvecco Modified Eagle Medium (DMEM) containing 10% fetal bovine serum (FBS), then the medium was replaced with DMEM medium containing 0.5% FBS. To this. unicellularized aloe not containing a preservative (2.0 wt % aqueous solution) or an ethanol extract of aloe (2.0 wt % aqueous solution) was added and the mixture was incubated for 48 hours. After the incubation ended, the procollagen type I carboxy terminal propeptide (PIP) produced by the human skin fibroblasts incubated was measured by the ELISA method. The amount of PIP of a unicellularized aloe added sample of a concentration of $10^{-3}$% by weight, when the amount of PIP per DNA of a sample to which unicellularized aloe was not added (control) was used as 100, was measured and used as the rate of promotion of collagen production (%).

Figure 12:
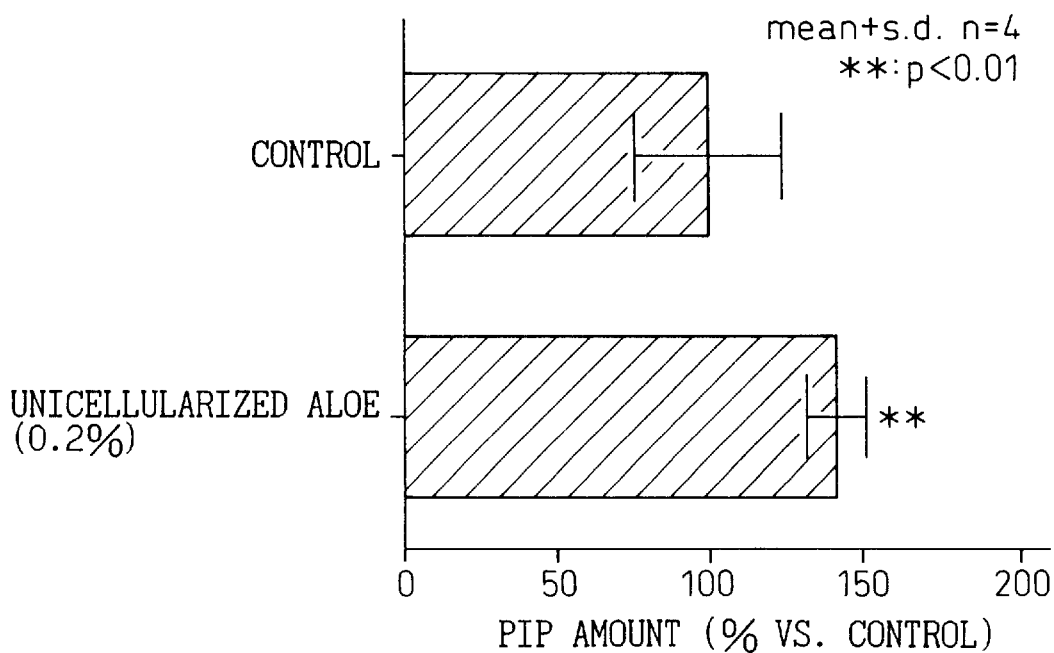
FIG. 12 is a view of a study on the effect of promotion of production of collagen by unicellularized aloe.

The results are shown in FIG. 12. Note that in FIG. 12, the horizontal axis shows the rate of promotion of collagen production (%) (=amount of PIP compared with control (%)).

From FIG. 12, it becomes. clear that the action of promotion of collagen production in human skin fibroblasts is observed in a significant extent in unicellularized aloe.

Test Example C1

Study of Moisture Retention Effect of Unicellularized Freesia Flower

The moisture retention effect of unicellularized Freesia flower (5 wt % aqueous solution) was studied in comparison with water and one of the leading humectants, glycerin (5 wt % aqueous solution).

Note that the method of study of the moisture retention effect was the same as the method performed in the above Test Example A2.

Figure 13:
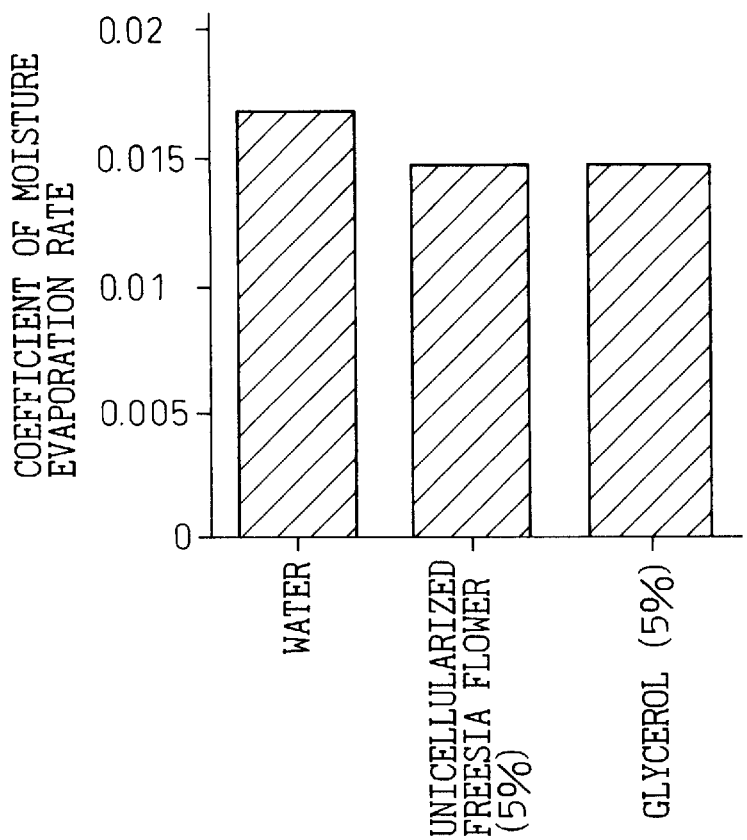
FIG. 13 is a view of a study of the moisture retention effect of unicellularized Freesia flower.

FIG. 13 shows the results of this test.

From the results, it becomes clear that, in relation with water, the same moisture retention effect is observed with the same concentration of a glycerin aqueous solution.

Test Example C2

Figure 14:
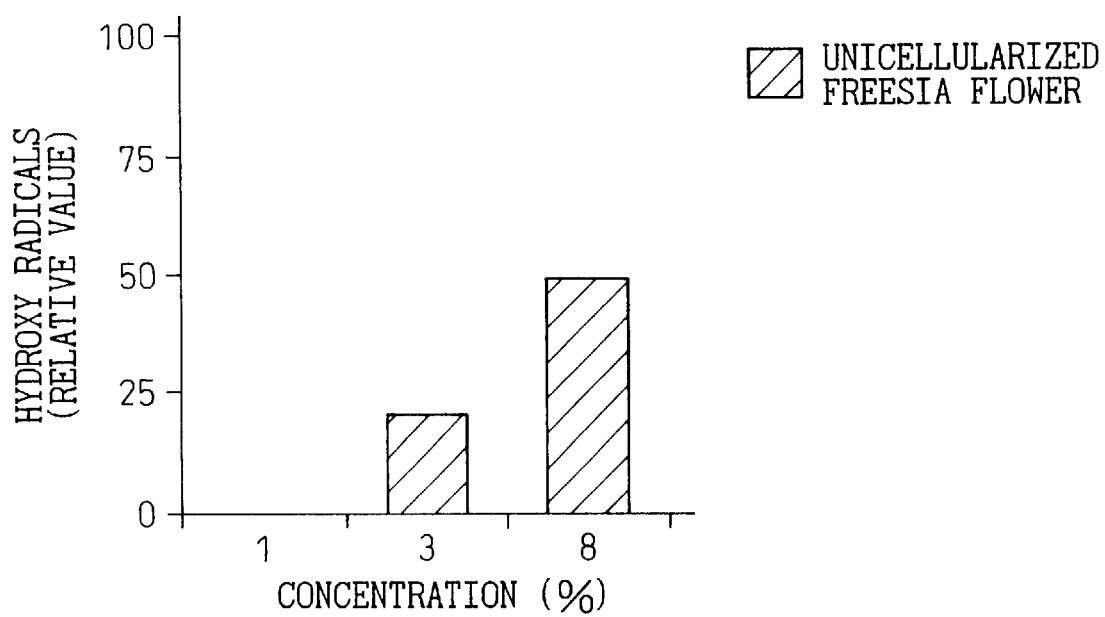
FIG. 14 is a view of a study of the effect of elimination of hydroxy radicals (OH.) in unicellularized Freesia flower.

Study of Effect of Elimination of Hydroxy Radicals (OH.) in Unicellularized Freesia Flower A study was conducted of the effect of elimination OH. in unicellularized Freesia flower prepared in Reference Example C (FIG. 14).

Note that the study of the effect of elimination of OH. was conducted by the ESR spin trapping method in the same way as in the above Test Example A4.

From FIG. 14, it is clear that unicellularized Freesia flower can exhibit the effect of elimination of OH. in proportion to the amount present.

Test Example D1

Study of Moisture Retention Effect of Unicellularized Iris Rhizome

The moisture retention effect of unicellularized iris rhizome was studied in comparison with purified water, glycerol, and an ethanol extract of iris rhizome.

That is, with the exception of the purified water, a 50 wt % aqueous solution was prepared and the coefficient of the moisture evaporation rate was found in the same way as the study of the moisture retention effect of unicellularized carrot (Test Example A2).

The results are shown in the following Table 1.

TABLE 1

| Sample | Coefficient of moisture evaporation rate |
|---|---|
| Unicellularized iris rhizome | −0.0189 |
| Ethanol extract of iris rhizome | −0.0249 |
| Purified water | −0.0254 |
| Glycerol | −0.0230 |

From the results of Table 1, the facts that the moisture retention effect of the unicellularized iris rhizome is superior to that of even glycerol and that the moisture retention effect is derived from the unicellularized iris rhizome are clear from the fact that not that great a moisture retention effect could be observed in the ethanol extract of the iris rhizome.

Examples A1 to A3

Cosmetic water of the formulations including unicellularized iris bulb shown in the following Table 2 were prepared by ordinary methods. First, the waters were subjected to tests of actual use, tests on light stability, and tests on moisture retention (the test methods, test results, etc. will be discussed later).

TABLE 2

| | Comp. Ex. | | | | | Ex. | | |
|---|---|---|---|---|---|---|---|---|
| | A1 | A2 | A3 | A4 | A5 | A1 | A2 | A3 |
| Purified water | Bal | Bal | Bal | Bal | Bal | Bal | Bal | Bal |
| Ethanol | 5.0 | 5.0 | 5.0 | 5.0 | 5.0 | 5.0 | 5.0 | 5.0 |
| Glycerol | 1.0 | 1.0 | 1.0 | 1.0 | 1.0 | 1.0 | 1.0 | 1.0 |
| Dipropylene glycol | 3.0 | 3.0 | 3.0 | 3.0 | 3.0 | 3.0 | 3.0 | 3.0 |
| Carboxy vinyl polymer | 0.1 | 0.1 | 0.1 | 0.1 | 0.1 | 0.1 | 0.1 | 0.1 |
| Diisostearic acid glycerol | 0.5 | 0.5 | 0.5 | 0.5 | 0.5 | 0.5 | 0.5 | 0.5 |
| Oleyl ether (15 mol) | 0.5 | 0.5 | 0.5 | 0.5 | 0.5 | 0.5 | 0.5 | 0.5 |
| Methylparabenzoate | 0.1 | 0.1 | 0.1 | 0.1 | 0.1 | 0.1 | 0.1 | 0.1 |
| Unicellularized carrot (freeze dried) | — | — | — | — | — | 1.0 | 3.0 | 5.0 — |
| Ethanol extract of carrot | — | 0.3 | 0.5 | — | — | — | — | 5.0 |
| β-carotene | — | — | — | 0.01 | 0.06 | — | — | |

Test of Actual Use

Tests on actual use were conducted on the external skin treatment compositions of the above formulations.

That is, suitable amounts of the above skin application agents were applied to the cheeks of the faces of a panel of women comprised of groups of 10 each to test the effect of improvement of the skin in actual use.

Criteria for Evaluation of Effects on Improvement of Skin
  EG: Extremely good (at least nine of 10 women evaluated sample as good)

G: Good (seven to eight of 10 women evaluated sample as good)

SG: Somewhat good (three to six of 10 women evaluated sample as good)

P: Poor (Less than two of 10 women evaluated sample as good).

The results are shown in Table 3.

TABLE 3

|  | Comp. Ex. | | | | | Ex. | | |
| --- | --- | --- | --- | --- | --- | --- | --- | --- |
|  | A1 | A2 | A3 | A4 | A5 | A1 | A2 | A3 |
| Effect on skin improvement | P | P | P | P | P | G | G | EG |

From these results, it is clear that by formulating the unicellularized carrot, it is possible to impart a skin improvement effect to the external skin treatment composition.

Note that in the Comparative Example, not only Comparative Example A1 which does not include any methanol extract of carrot or β-carotene at all, but also the other Comparative Examples, where one of the same is formulated, showed no effect on improvement of the skin at all.

That is, the skin improvement effect of the above Examples is strongly suggested to be not an effect derived from β-carotene, but an effect due to the formulating of the unicellularized plant (for example, the possibility that the cell walls of the single cell plants are relevant etc.)

Test on Stability Against Light

Products which had been exposed to sunlight at 0° C. were measured as to the Hunter color difference (ΔE) by an SM color computer using the transmitted light and, at the same time, judgement was performed by the naked eye:

$$\Delta E(L_{ab}) = [(\Delta L)^2 + (\Delta a)^2 + (\Delta b)^2]^{1/2}$$

Criteria for Judgement by Naked Eye

EG to G: No problem (Extent of color fading lesser in EG than G)

SG: Within allowable range

P: Fading

The results are shown in Table 4.

TABLE 4

|  | 1 day | 3 days | 6 days | 8 days | Remarks |
| --- | --- | --- | --- | --- | --- |
| Ex. A3 | 0.28 G | 1.00 G | 1.31 SG | 2.57 P | unicellularized carrot |
| Comp. Ex. A1 | 0.18 G | 0.35 G | 0.83 G | 2.29 G | None (control) |
| Comp. Ex. A5 | 0.38 G | 1.84 G | 7.54 P | 4.73 P | β-carotene |

From these results, it is found that the external skin treatment composition of the present invention in Example A3 where the unicellularized carrot is formulated has less of a degree of fading of color of the β-carotene along with time compared with Comparative Example A5 in which β-carotene is formulated in another form. From this, it is learned that in the external skin treatment composition of the present invention in which the unicellularized plant is formulated, it i possible to suppress spoilage of effective ingredients in the plant along with time.

Note that the above results were obtained in Example A3 where the amount of formulating of the unicellularized carrot was the greatest, so it is clear that in Example A1 and Example A2 where the amount of formulating of the uni- cellularized carrot is smaller and, as a result, the amount of formulating of the β-carotene unstable against light and heat is smaller, there is a greater effect of preventing of fading due to the unicellularization exhibited than even Example A3.

Test of Temperature Stability

The Hunter color difference (ΔE) in the case of allowing a sample to stand for 8 days at 37° C. and 50° C., compared against 0° C., was measured. At the same time, judgement was made by the naked eye.

Criteria for Judgement by Naked Eye

G: No problem

SG: Within allowable range

P: Fading

The results are shown in Table 5.

TABLE 5

|  | 37° C. | 50° C. | Remarks |
| --- | --- | --- | --- |
| Ex. A8 | 1.01 G | 1.03 G |  |
| Comp. Ex. A1 | 7.54 G | 4.96 G | Difficult to see since becoming cloudy white |
| Comp. Ex. A5 | 5.55 P | 8.24 P |  |

From these results, it is found that almost no color fading could be observed at all in the external skin treatment composition of the present invention even under tough conditions of 50° C.

Note that in Example A1 and Example A2 where the amount of the unicellularized carrot formulated was smaller, due to the same reasons as explained regarding the above test of the light stability, a temperature stability greater than that of Example A3 can be observed.

Moisture Retention test

The moisture retention of the external skin treatment composition was studied by the same test system as with the moisture retention test of the above unicellularized plants Example A1, Comparative Example A1, Comparative Example A5.

Figure 15:
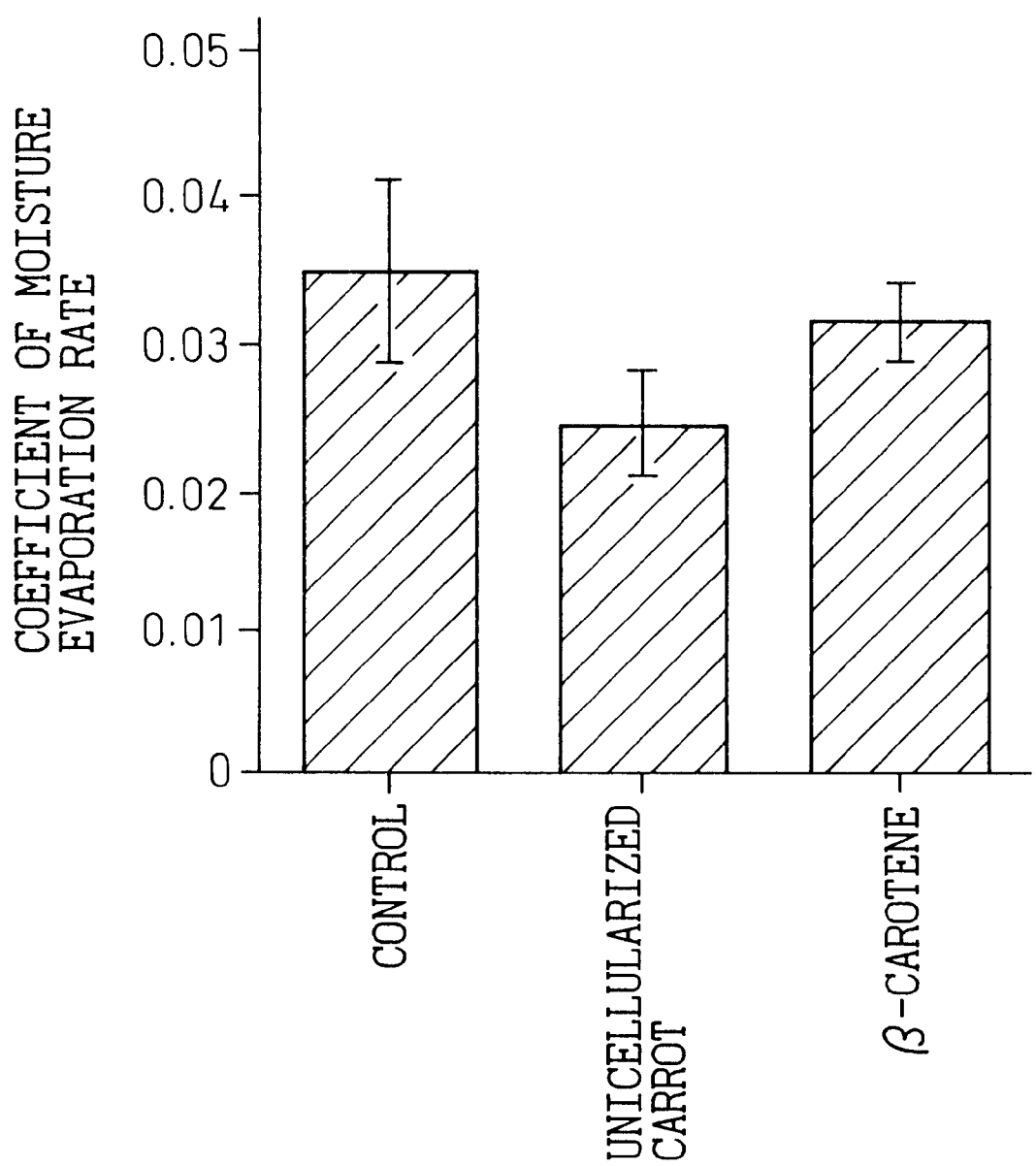
FIG. 15 is a view of a study of the moisture retention effect of the external skin treatment composition of the present invention.

The results are shown in FIG. 15.

From the figure, it is clear that there is a superior moisture retention effect in the external skin treatment composition of the present invention.

Note that in Example A2 and Example A3, which have greater amounts of the unicellularized carrot formulated than Example A1, it should be clear that a moisture retention effect greater than Example A1 can be observed.

Below, examples of the ingredients of various formulations of the external skin treatment composition of the present invention are described. Note that the same tests as with the above Examples A1 to A3 were conducted on the formulations, whereupon it was found that all of the formulations were superior in usability, stability against light, stability against humidity, and moisture retention.

Example A4

Translucent Cosmetic Water

|  | wt % |
| --- | --- |
| Ethanol | 8.0 |
| Polyester glycol 1500 | 2.0 |
| Glycerol | 1.0 |
| Dipropylene glycol | 5.0 |
| Carboxyvinyl polymer | 0.1 |
| Potassium hydroxide | 0.1 |

-continued

| | wt % |
|---|---|
| L-alginin | 0.05 |
| Pentaerythritol-tetra-2-ethylhexanoate | 1.0 |
| 2-hydroxy-4-methoxybenzophenon | 0.1 |
| Unicellularized carrot (freeze dried product) | 3.0 |
| Purified water | Balance |

Method of Preparation

The translucent toilet water was produced by an ordinary method.

Example A5

Emulsion

| | wt % |
|---|---|
| Carboxyvinyl polymer | 0.05 |
| Potassium hydroxide | 0.3 |
| Stearic acid | 1.5 |
| Cetyl alcohol | 0.5 |
| Squalane | 5.0 |
| Beeswax | 1.0 |
| Polyoxyethylene(10 mol)monooleic acid ester | 1.0 |
| PCA-Na | 0.05 |
| L-alginin | 0.1 |
| Glycerol | 3.0 |
| Dipropylene glycol | 3.0 |
| Unicellularized carrot (freeze dried product) | 5.0 |
| Purified water | Balance |

Method of Preparation

The above aqueous phase ingredients and oil phase ingredients were mixed and emulsified and then an ordinary method was used to obtain the desired emulsion.

Example A6

Cosmetic Water

| | wt % |
|---|---|
| Glycerol | 5.0 |
| Citric acid | 0.03 |
| Sodium citrate | 0.05 |
| Unicellularized carrot (freeze dried product) | 0.1 |
| Ethanol (95%) | 10.0 |
| POE(15 mol)oleyl ester | 1.0 |
| D-glucosamine hydrochloride | 1.0 |
| UV absorbant | 0.1 |
| Perfume | 0.1 |
| Preservative | 0.1 |
| Color | q.s. |
| Purified water | Balance |

Method of Preparation

Ethanol (95%), POE(15 mol)oleyl ester, perfume, and the preservative were mixed and dissolved with each other at room temperature, then added with stirring, in a similarly room temperature mixed and dissolved glycerin, citric acid, sodium citrate, unicellularized carrot (freeze dried product), D-glucosamine hydrochloride, the UV absorbant, color, and purified water to obtain the desired toilet water.

Example A7

W/O Type Cream

| | wt % |
|---|---|
| Glycerol | 5.0 |
| Polyethylene glycol (M.W. 400) | 2.0 |
| Glycyrrhetinic acid monoammonium salt | 0.1 |
| Unicellularized carrot (freeze-dried product) | 0.1 |
| N-acetyl-D-glucosamin | 10.0 |
| Cetanol | 4.0 |
| Squalane | 5.0 |
| Stearic acid | 1.0 |
| Beeswax | 1.0 |
| Vaseline | 1.0 |
| POE(25 mol)cetyl ether | 2.0 |
| Glyceryl monostearate | 1.5 |
| Preservative | 0.1 |
| Perfume | 0.15 |
| Purified water | Balance |

Method of Preparation

The N-acetyl-D-glucosamin, cetanol, squalane, stearic acid, beeswax, vaseline, POE(25 mol)cetyl ether, glyceryl monostearate, preservative, and perfume were mixed and dissolved in each other and then were mixed and emulsified, with stirring, in the similarly mixed and dissolved glycerol, polyethylene glycol, glycyrrhetinic acid monoammonium salt, unicellularized carrot, and purified water. The emulsified particles were homogenated by a homogenizer and then the mixture was cooled to room temperature by a heat exchanger to obtain the desired W/O type cream.

Example A8

Pack

| | wt % |
|---|---|
| Polyvinyl alcohol | 10.0 |
| Polyethylene glycol (M.W. 400) | 0.4 |
| Glycerol | 3.0 |
| Ethanol (95%) | 8.0 |
| Unicellularized carrot (freeze-dried product) | 0.1 |
| Preservative | 0.1 |
| Perfume | 0.1 |
| Purified water | Balance |

Method of Preparation

The ethanol, unicellularized carrot, preservative, and perfume were mixed and dissolved in each other, then added, with stirring, into polyvinyl alcohol, polyethylene glycol, glycerol, and perfume mixed and dissolved at 80° C. The mixture was allowed to cool to room temperature to obtain the desired pack.

Example A9

Stick-Shaped Lipstick

|  | wt % |
|---|---|
| Castor oil | 20.0 |
| Cetyl alcohol | 20.0 |
| Beeswax | 5.0 |
| Candelilla wax | 30.0 |
| Unicellularized carrot (freeze-dried product) | 2.0 |
| Squalane | 13.0 |
| Carnauba wax | 5.0 |
| Pigment | 5.0 |
| Perfume | q.s. |

Method of Preparation

The above ingredients were mixed and dissolved at 80° C., poured into a mold, and allowed to cool to room temperature, then the result was taken out to obtain the desired stick-shaped lipstick.

Example A10

Hair Rinse

|  | wt % |
|---|---|
| Chlorinated alkyl trimethyl ammonium | 3.0 |
| Cetyl alcohol | 1.0 |
| Unicellularized carrot (freeze-dried product) | 2.0 |
| Preservative | 0.1 |
| Glycerol | 5.0 |
| Perfume | 0.1 |
| Color | q.s. |
| POE(8 mol)stearyl ether | 0.6 |
| Purified water | Balance |

Method of Preparation

The above ingredients were mixed and dissolved at 80° C., then allowed to cool to room temperature to obtain the desired hair rinse.

Example A11

Hair Tonic

|  | wt % |
|---|---|
| Ethanol (95%) | 50.0 |
| Glycerol | 1.0 |
| POE(80 mol)hydrogenated castor oil ether | 1.0 |
| Perfume | 0.5 |
| Unicellularized carrot (freeze-dried product) | 0.005 |
| Hinoki oil | 0.005 |
| Purified water | Balance |

Method of Preparation

The ethanol, POE(60 mol)hydrogenated castor oil ether, perfume, unicellularized carrot, and hinoki oil were dissolved, with stirring, at ordinary temperature, then the glycerol and purified water were added to this, with stirring, to obtain the desired hair tonic.

Example A12

Powdery Foundation

|  | wt % |
|---|---|
| Sericite | 47.28 |
| Talc | 15.0 |
| Unicellularized carrot (freeze-dried product) | 15.0 |
| Titanium dioxide | 6.5 |
| Iron oxide | 3.5 |
| Trimethylolpropanetriisostearate | 5.0 |
| Squalane | 6.0 |
| Sorbitan sesquioleate | 1.0 |
| Preservative | 0.5 |
| Antioxidant | 0.02 |
| Perfume | 0.2 |

Method of Preparation

The powdery foundation was produced by an ordinary method.

Example A13

Stick Eyeshadow

|  | wt % |
|---|---|
| Prussian Blue | 12.0 |
| Talc | 4.0 |
| Unicellularized carrot (freeze-dried product) | 5.0 |
| Pearl powder | 17.0 |
| Carnauba wax | 10.0 |
| Solid paraffin | 5.0 |
| Lanolin derivative | 5.0 |
| Squalane | 21.0 |
| Glyceryl tri-2-ethylhexanic acid ester | 20.0 |
| Sorbitan sesquioleic acid ester | 1.0 |
| Perfume | q.s. |

Method of Preparation

This stick eyeshadow was produced by an ordinary method.

Example A14

Cleansing Cream

|  | wt % |
|---|---|
| Cetanol | 2.0 |
| Beeswax | 2.0 |
| Stearic acid | 3.0 |
| Vaseline | 8.0 |
| Squalane | 37.0 |
| Isopropyl myristate | 10.0 |
| POE(20 mol)sorbitan lauric acid ester | 2.5 |
| Glycerine monostearate | 2.5 |
| Ethylparabenzoate | 0.3 |
| Perfume | 0.2 |
| Glycerol | 2.0 |
| Propylene glycol | 5.0 |
| Purified water | Balance |

-continued

| | wt % |
|---|---|
| Potassium hydroxide | 0.1 |
| Unicellularized carrot (freeze-dried product) | 5.0 |

Method of Preparation

The cetanol, beeswax, stearic acid, vaseline, squalane, isopropyl myristate, POE(20 mol)sorbitan lauric acid ester, glycerol monostearate, ethylparabenzoate, and perfume and the glycerol, propylene glycol, purified water, potassium hydroxide, and unicellularized carrot were respectively heated to 70° C. and melted, then the former oil phase ingredients were added to the latter aqueous phase ingredients and the two were emulsified using an emulsifier, then the result was cooled to 30° C. by a heat exchanger. This was filled into a container to obtain the desired cleansing cream.

Example A15

Calamine Lotion

| | wt % |
|---|---|
| Calamine | 1.0 |
| Unicellularized carrot (freeze-dried product) | 1.0 |
| Bentonite | 0.2 |
| Phenol | q.s. |
| Glycerol | 4.0 |
| Purified water | Balance |

Method of Preparation

The calamine lotion was produced by an ordinary, method.

Example A16

Solid Powder

| | wt % |
|---|---|
| Talc | 87.9 |
| Unicellularized carrot (freeze-dried product) | 10.0 |
| Liquid paraffin | 2.0 |
| Perfume | 0.1 |

Method of Preparation

The solid power was produced by an ordinary method.

Example A17

Rouge

| | wt % |
|---|---|
| Unicellularized carrot (freeze-dried product) | 5.0 |
| Talc | 80.0 |
| Zinc stearate | 5.0 |

-continued

| | wt % |
|---|---|
| Rice starch | 10.0 |
| Pigment | q.s. |
| Perfume | q.s. |
| Preservative | q.s. |

Method of Preparation

This rouge was produced by an ordinary method.

Example A18

Eyeliner

| | wt % |
|---|---|
| Iron oxide (black) | 11.0 |
| Unicellularized carrot (freeze-dried product) | 5.0 |
| Vinyl acetate resin emulsion | 43.0 |
| Glycerol | 5.0 |
| POE(20 mol)sorbitan monooleic acid ester | 1.0 |
| Carboxyethylenemethylcellulose (10% aqueous solution) | 15.0 |
| Acetyltributyl citrate | 1.0 |
| Purified water | 19.0 |
| Perfume | q.s. |
| Preservative | q.s. |

Method of Preparation

This eyeliner was produced by an ordinary method.

Example A19

After Shave Lotion

| | wt % |
|---|---|
| Ethanol (95%) | 25.0 |
| Sorbitol | 2.0 |
| Hexachlorophene | 0.1 |
| Menthol | 0.3 |
| Aminobenzoic acid | 0.2 |
| Citric acid | 0.1 |
| Perfume | q.s. |
| Unicellularized carrot (freeze-dried product) | 0.1 |
| Purified water | Balance |

Method of Preparation

This after shave lotion was produced by an ordinary method.

Example A20

Beautify Liquid

| | wt % |
|---|---|
| Glycerol | 8.0 |
| Dipropylene glycol | 5.0 |

-continued

| | wt % |
|---|---|
| Hyaluronic acid | 0.1 |
| Ethanol | 5.0 |
| Carboxyvinyl polymer | 0.15 |
| Potassium hydroxide | 0.006 |
| Sodium hexametaphosphate | 0.02 |
| Urocanic acid | 0.1 |
| Pantothenylethylether | 0.05 |
| Perfume | 0.01 |
| POE(20 mol)octyldodecanol | 0.3 |
| Methylparabenzoate | 0.1 |
| Trisodium edetate | 0.01 |
| Unicellularized carrot (freeze-dried product) | 1.0 |
| Purified water | Balance |

Method of Preparation

This beauty liquid was produced by an ordinary method.

Example A21

Emulsion

| | wt % |
|---|---|
| Squalane | 5.0 |
| Vaseline | 2.0 |
| Beeswax | 0.5 |
| Sorbitan sesquioleyl ester | 0.8 |
| 20(EO)polyoxyethylene oleyl ether | 1.2 |
| Perfume | 0.5 |
| Ethylparabenzoate | q.s. |
| Vitamin E acetate | q.s. |
| Propylene glycol | 5.0 |
| Hyaluronic acid | 0.5 |
| Ethanol | 5.0 |
| Carboxyvinyl polymer (1.0 wt % aqueous solution) | 20.0 |
| Potassium hydroxide | 0.1 |
| Unicellularized carrot (freeze-dried product) | 1.0 |
| Purified water | Balance |

Method of Preparation

The emulsion was prepared by an ordinary method.

Example A22

Hair-Use Acidic Hair Dye

| | wt % |
|---|---|
| Black No. 401 | 0.2 |
| Violet No. 401 | 0.3 |
| Yellow No. 4 | 0.1 |
| Benzyl alcohol | 5.0 |
| Xanthane gum | 1.0 |
| Citric acid | 0.5 |
| Trisodium ethylene diamine tetraacetate | q.s. |
| Unicellularized carrot (freeze-dried product) | 1.0 |
| Purified water | Balance |

Method of Preparation

The benzyl alcohol was added to the purified water, then the xanthane gum, citrate acid, trisodium ethylene diamine tetraacetate, and unicellularized carrot were gradually added to prepare a viscous solution. To this viscous solution were added Black No. 401, Violet No. 401, and Yellow No. 4. These were mixed homogeneously with stirring to obtain the desired hair acidic hair dye.

Example A23

Rinse-in Shampoo

| | wt % |
|---|---|
| Sodium laurylpolyoxyethylene (3 mol) sulfuric acid ester | 9.0 |
| Sodium lauryl sulfuric acid ester | 4.0 |
| Coconut oil fatty acid diethanol amide | 4.0 |
| Glycerol | 1.0 |
| Unicellularized carrot (freeze-dried product) | 0.2 |
| Lactic acid | 0.5 |
| Perfume | q.s. |
| Color | q.s. |
| Trisodium ethylene amide tetraacetate | q.s. |
| Purified water | Balance |

Method of Preparation

The unicellularized carrot, lactic acid, perfume, color, and trisodium ethylene diamine tetraacetate were gradually added and mixed with stirring, then the mixture was heated to 70° C. and the sodium laurylpolyoxyethylene (3 mol) sulfuric acid ester, sodium lauryl sulfuric acid ester, coconut oil fatty acid diethanol amide, and glycerol were added and mixed with stirring. The mixture was then cooled to 30° C. to obtain the desired rinse shampoo.

Example A24

Body Shampoo

| | wt % |
|---|---|
| Coconut oil | 10.0 |
| Beef tallow | 5.0 |
| Lauric acid | 5.0 |
| Myristic acid | 4.0 |
| Methylpolysiloxane | 0.5 |
| Propylene glycol | 10.0 |
| 1,3-butylene glycol | 5.0 |
| Acetic acid-dl-α-tocopherol | 0.05 |
| Potassium hydroxide | 5.0 |
| Methyl cellulose | 0.5 |
| Trisodium ethylene diamine tetraacetate | 0.1 |
| Unicellularized carrot (freeze-dried product) | 0.5 |
| Phosphoric acid | 0.3 |
| Perfume | q.s. |
| Purified water | Balance |

Method of Preparation

The coconut oil, beef tallow, lauric acid, myristic acid, methyl polysiloxane, propylene glycol, 1,3-butylene glycol, and acetic acid-dl-α-tocopherol were heated to dissolve then added to the potassium hydroxide, then the purified water into which had been dissolved the methyl cellulose, trisodium ethylene diamine tetraacetate, unicellularized carrot, phosphoric acid, and perfume was added to this and the two mixed with stirring to obtain the desired body shampoo.

Example A25

Body Rinse

| | wt % |
|---|---|
| 1,3-butylene glycol | 15.0 |
| POP(9 mol)diglyceryl ether | 15.0 |
| Dipropylene glycol | 10.0 |
| Carboxy vinyl polymer | 0.5 |
| Xanthane gum | 0.5 |
| Methyl p-oxybenzoate | 0.1 |
| Methyl polysiloxane | 5.0 |
| Perfume | q.s. |
| Unicellularized carrot (freeze-dried product) | 0.6 |
| Lactic acid | 0.3 |
| Purified water | Balance |

Method of Preparation

To the purified water were dissolved the 1,3-butylene glycol, POP(9 mol)diglyceryl ether, dipropylene -glycol, carboxyvinyl polymer xanthane gum, and methyl p-oxybenzoate. To this was added the methyl polysiloxane and perfume. These were mixed with stirring, then the unicellularized carrot and lactic acid were added to obtain the desired body rinse.

Example B1

Cream

| | wt % |
|---|---|
| Stearic acid | 5.0 |
| Stearyl alcohol | 4.0 |
| Isopropyl myristate | 18.0 |
| Glycerol monostearic acid ester | 3.0 |
| Propylene glycol | 10.0 |
| Unicellularized aloe (freeze-dried product) | 0.5 |
| Potassium hydroxide | 0.2 |
| Sodium hydrosulfite | 0.01 |
| Preservative | q.s. |
| Perfume | q.s. |
| Purified water | Balance |

Method of Preparation

To the purified water were added and dissolved the propylene glycol, unicellularized aloe, and potassium hydroxide. This was heated and held at 70° C. (aqueous phase). Separate from this, the other ingredients were mixed and heated to melt and held at 70° C. (oil phase). The oil phase was gradually added to the above aqueous phase. For a while after the entire amount finished being added, the mixture was held at 70° C. to cause the reaction. Next, a homogenizer was used to emulsify the mixture homogeneously. This was cooled down to 30° C. with strong stirring to obtain the desired cream.

Example B2

Cream

| | wt % |
|---|---|
| Stearic acid | 2.0 |
| Stearyl alcohol | 7.0 |
| Hydrogenated lanolin | 2.0 |
| Squalane | 5.0 |
| 2-octyldodecyl alcohol | 6.0 |
| Polyoxyethylene(25 mol)cetyl alcohol ether | 3.0 |
| Glycerol monostearic acid ester | 2.0 |
| Propylene glycol | 5.0 |
| Unicellularized aloe (freeze-dried product) | 1.0 |
| Sodium hydrosulfite | 0.03 |
| Ethylparabenzoate | 0.3 |
| Perfume | q.s. |
| Purified water | Balance |

Method of Preparation

The propylene glycol was added to the purified water, then these were heated and held at 70° C. (aqueous phase). Separate from this, the other ingredients were mixed and heated to melt then held at 70° C. (oil phase). The oil phase was added to the aqueous phase, preliminary emulsification was performed, then the result was emulsified homogeneously by a homomixer and cooled down to 30° C. with vigorous stirring to obtain the desired cream.

Example B3

Cream

| | wt % |
|---|---|
| Solid paraffin | 5.0 |
| Beeswax | 10.0 |
| Vaseline | 15.0 |
| Liquid paraffin | 41.0 |
| Glycerol monostearic acid ester | 2.0 |
| Polyoxyethylene(20 mol)sorbitan monolauric acid ester | 2.0 |
| Soap powder | 0.1 |
| Borax | 0.2 |
| Unicellularized aloe (freeze-dried product) | 1.0 |
| Sodium hydrosulfite | 0.03 |
| Ethylparabenzoate | 0.3 |
| Perfume | q.s. |
| Purified water | Balance |

Method of Preparation

The soap powder and sodium borate were added to the purified water, then the mixture was heated to dissolve them and held at 70° C. (aqueous phase). Separately from this, the other ingredients were mixed and heated to melt at 70° C. (oil phase). The oil phase was gradually added, with stirring to the aqueous phase to cause the reaction. After the end of the reaction, a homomixer was used to homogeneously emulsify the mixture which was then cooled with stirring to obtain the desired cream.

Example B4

Emulsion

| | wt % |
|---|---|
| Stearic acid | 2.5 |
| Cetyl alcohol | 1.5 |
| Vaseline | 5.0 |
| Liquid paraffin | 10.0 |
| Polyoxyethylene(10 mol)monooleic acid ester | 2.0 |
| Polyethylene glycol 1500 | 3.0 |
| Triethanol amine | 1.0 |
| Carboxy vinyl polymer (brand name: Carbopol 941, made by B. F. Goodrich) | 0.05 |
| Unicellularized aloe (freeze-dried product) | 0.5 |
| Sodium hydrosulfite | 0.01 |
| Ethylparabenzoate | 0.3 |
| Perfume | q.s. |
| Purified water | Balance |

Method of Preparation

The carboxy vinyl polymer was dissolved in a small amount of purified water (phase A). The polyethylene glycol 1500 and triethanol amine were added to the remaining purified water which was then heated to dissolve the same and held at 70° C. (aqueous phase). The other ingredients were mixed and heated to melt and then held at 70° C. (oil phase). The oil phase was added to the aqueous phase and preliminary emulsification performed, then the phase A was added and a homomixer was used for homogeneous emulsification. After the emulsification, the mixture was stirred vigorously to obtain the desired emulsion.

Example B5

Emulsion

| | wt % |
|---|---|
| Microcrystalline wax | 1.0 |
| Beeswax | 2.0 |
| Lanolin | 20.0 |
| Liquid paraffin | 10.0 |
| Squalane | 5.0 |
| Sorbitan sesquioleic acid ester | 4.0 |
| Polyoxyethylene(20 mol)sorbitan monooleic acid ester | 1.0 |
| Propylene glycol | 7.0 |
| Unicellularized aloe (freeze-dried product) | 10.0 |
| Sodium hydrosulfite | 0.01 |
| Ethylparabenzoate | 0.3 |
| Perfume | q.s. |
| Purified water | Balance |

Method of Preparation

The polypropylene glycol was added to the purified water which was then heated and held at 70° C. (aqueous phase). Separate from this, the other ingredients were mixed and heated to melt and held at 70° C. (oil phase). The oil phase was gradually added to the aqueous phase while stirring and a homomixer was used to homogeneously emulsify the two. After the emulsification, the mixture was cooled to 30° C. with vigorous stirring to obtain the desired emulsion.

Example B6

Gel

| | wt % |
|---|---|
| 95% ethyl alcohol | 10.0 |
| Dipropylene glycol | 15.0 |
| Polyoxyethylene(50 mol)oleyl alcohol ester | 2.0 |
| Carboxy vinyl polymer (brand name: Carbopol 940, made by G. F. Goodrich) | 1.0 |
| Potassium hydroxide | 0.15 |
| L-arginine | 0.1 |
| Unicellularized aloe (freeze-dried product) | 5.0 |
| Sodium 2-hydroxy-4-methoxybenzophenone sulfonate | 0.05 |
| 3-sodium-2-hydrogen ethylene diamine tetraacetate | 0.05 |
| Methylparabenzoate | 0.2 |
| Perfume | q.s. |
| Purified water | Balance |

Method of Preparation

The Carbopol 940 was homogeneously dissolved in the purified water (aqueous phase). On the other hand, the unicellularized aloe, polyoxyethylene(50 mol)oleyl alcohol ether were dissolved in the 95% ethanol and added to the aqueous phase. Next, the other ingredients were added to the aqueous phase, then the mixture was neutralized and thickened by the potassium hydroxide and the L-arginine to obtain the desired gel.

Example B7

Beauty Liquid

| | wt % |
|---|---|
| (phase A) | |
| 95% ethyl alcohol | 10.0 |
| Polyoxyethylene(20 mol)octyldodecanol | 1.0 |
| Pantothenylethyl ether | 0.1 |
| Unicellularized aloe (freeze-dried product) | 2.0 |
| Methylparabenzoate | 0.15 |
| (phase B) | |
| Potassium hydroxide | 0.1 |
| (phase C) | |
| Glycerol | 5.0 |
| Dipropylene glycol | 10.0 |
| Sodium hydrosulfite | 0.03 |
| Carboxy vinyl polymer (brand name: Carbopol 940, made by B. F. Goodrich) | 0.2 |
| Purified water | Balance |

Method of Preparation

The phase A and the phase C were homogeneously dissolved then the phase A was added to the phase C to solubilize it. Next, the phase B was added, then the mixture was filled in the containers.

Example B8

Pack

| | wt % |
|---|---|
| (phase A) | |
| Dipropylene glycol | 5.0 |
| Polyoxyethylene(60 mol)hydrogenated castor oil | 5.0 |
| (phase B) | |
| Unicellularized aloe (freeze-dried product) | 0.1 |
| Olive oil | 5.0 |
| Tocopheryl acetate | 0.2 |
| Ethylparabenzoate | 0.2 |
| Perfume | 0.2 |
| (phase C) | |
| Sodium hydrogensulfite | 0.03 |
| Polyvinyl alcohol (saponification 90, polymerization degree 2000) | 13.0 |
| Ethanol | 7.0 |
| Purified water | Balance |

Method of Preparation

The phase A, phase B, and phase C were all homogeneously dissolved, then the phase B was added to the phase A to solubilize it. Next, this was added to the phase C, followed by filling to obtain the desired pack.

Example B9

Solid Foundation

| | wt % |
|---|---|
| Talc | 43.1 |
| Kaolin | 15.0 |
| Sericite | 10.0 |
| Zinc white | 7.0 |
| Titanium dioxide | 3.8 |
| Yellow iron oxide | 2.9 |
| Black iron oxide | 0.2 |
| Squalane | 8.0 |
| Isostearic acid | 4.0 |
| Monooleic acid polyoxyethylene sorbitan | 3.0 |
| Isocetyl octanate | 2.0 |
| Unicellularized aloe (freeze-dried product) | 0.1 |
| Preservative | q.s. |
| Perfume | q.s. |

Method of Preparation

The powder components from the talc to the black iron oxide were fully mixed by a blender, then the oily ingredients of the squalane to isocetyl octanate, the unicellularized aloe, the preservative, and the perfume were added and kneaded well. The resultant mixture was filled into molds to obtain the desired solid foundation.

Example B10

Solid Foundation (Cream Type)

| | wt % |
|---|---|
| (Powder portion) | |
| Titanium dioxide | 10.03 |
| Sericite | 5.4 |
| Kaolin | 3.0 |
| Yellow iron oxide | 0.8 |
| Bengara | 0.3 |
| Black iron oxide | 0.2 |
| (Oil phase) | |
| Decamethylcyclopentasiloxane | 11.5 |
| Liquid paraffin | 4.5 |
| Polyoxyethylene modified dimethyl polysiloxane | 4.0 |
| (Aqueous phase) | |
| Purified water | 50.0 |
| 1,3-butylene glycol | 4.5 |
| Unicellularized aloe (freeze-dried product) | 1.5 |
| Sorbitan sesquioleic acid ester | 3.0 |
| Preservative | q.s. |
| Perfume | q.s. |

Method of Preparation

The aqueous phase was heated and stirred, then the powder portion, which was fully mixed and pulverized, was added to this and the two processed by a homomixer. The heated and mixed oil phase was added to this and the result processed by a homomixer, then -the perfume was added while stirring and the mixture cooled to room temperature to obtain the desired cream type solid foundation.

Example C1

Cream

| | wt % |
|---|---|
| Stearic acid | 5.0 |
| Stearyl alcohol | 4.0 |
| Isopropyl myristate | 18.0 |
| Glycerol monostearic acid ester | 3.0 |
| Propylene glycol | 10.0 |
| Unicellularized iris rhizome (freeze-dried product) | 0.1 |
| Potassium hydroxide | 0.2 |
| Sodium hydrosulfite | 0.01 |
| Preservative | q.s. |
| Perfume | q.s. |
| Purified water | Balance |

Method of Preparation

The propylene glycol, unicellularized iris rhizome, and potassium hydroxide were added to and dissolved in the purified water which was then heated and held at 70° C. (aqueous phase). Separate from this, the other ingredients were mixed and heated to melt and were held at 70° C. (oil phase). The oil phase was gradually added to the above aqueous phase. After the entire amount had finished being added, the mixture was held for a while at 70° C. to cause the reaction. Next, a homomixer was used to homogeneously emulsify the mixture which was then cooled to 30° C. while vigorously stirring to obtain the desired cream.

Example C2

Cream

|  | wt % |
|---|---|
| Stearic acid | 2.0 |
| Stearyl alcohol | 7.0 |
| Hydrated lanolin | 2.0 |
| Squalane | 5.0 |
| 2-octyldodecyl alcohol | 6.0 |
| Polyoxyethylene(25 mol)cetyl alcohol ether | 3.0 |
| Glycerol monostearic acid ester | 2.0 |
| Propylene glycol | 5.0 |
| Unicellularized iris rhizome (freeze-dried product) | 2.0 |
| Sodium hydrosulfite | 0.03 |
| Ethylparabenzoate | 0.3 |
| Perfume | q.s. |
| Purified water | Balance |

Method of Preparation

The propylene glycol was added to the purified water which was then heated and held at 70° C. (aqueous phase). Separate from this, the other ingredients were mixed and the result heated to melt and held at 70° C. (oil phase). The oil phase was added to the aqueous phase and preliminary emulsification was performed, then a homomixer was used for homogeneous emulsification. Next, this was cooled to 30° C. with vigorous stirring to obtain the desired cream.

Example C3

Cream

|  | wt % |
|---|---|
| Solid paraffin | 5.0 |
| Beeswax | 10.0 |
| Vaseline | 15.0 |
| Liquid paraffin | 41.0 |
| Glycerol monostearic acid ester | 2.0 |
| Polyoxyethylene(20 mol)sorbitan monolauric acid ester | 2.0 |
| Soap powder | 0.1 |
| Sodium borate | 0.2 |
| Unicellularized iris rhizome (freeze-dried product) | 2.0 |
| Sodium hydrosulfite | 0.03 |
| Ethylparabenzoate | 0.3 |
| Perfume | q.s. |
| Purified water | Balance |

Method of Preparation

The soap powder and sodiumborate were added to the purified water which was then heated to dissolve them and held at 70° C. (aqueous phase). Separately from this, the other ingredients were mixed and heated to melt at 70° C. (oil phase). The oil phase was gradually added, with stirring, to the aqueous phase to cause the, reaction. After the end of the reaction, a homomixer was used to homogeneously emulsify the mixture which was vigorously stirred to obtain the desired cream.

Example C4

Emulsion

|  | wt % |
|---|---|
| Stearic acid | 2.5 |
| Cetyl alcohol | 1.5 |
| Vaseline | 5.0 |
| Liquid paraffin | 10.0 |
| Polyoxyethylene(10 mol)monooleic acid ester | 2.0 |
| Polyethylene glycol 1500 | 3.0 |
| Triethanol amine | 1.0 |
| Carboxy vinyl polymer (brand name: Carbopol 941, made by B. F. Goodrich) | 0.05 |
| Unicellularized aloe (freeze-dried product) | 0.1 |
| Sodium hydrosulfite | 0.01 |
| Ethylparabenzoate | 0.3 |
| Perfume | q.s. |
| Purified water | Balance |

Method of Preparation

The carboxy vinyl polymer was dissolved in a small amount of purified water (A phase). The polyethylene glycol 1500 and triethanol amine were added to the remaining purified water which was then heated to dissolve the same and held at 70° C. (aqueous phase). The other ingredients were mixed and heated to melt them and then held at 70° C. (oil phase). The oil phase was added to the aqueous phase and preliminary emulsification performed, then the phase A was added and a homomixer was used for homogeneous emulsification. After the emulsification, the mixture was stirred vigorously to obtain the desired emulsion.

Example C5

Emulsion

|  | wt % |
|---|---|
| Microcrystalline wax | 1.0 |
| Beeswax | 2.0 |
| Lanolin | 20.0 |
| Liquid paraffin | 10.0 |
| Squalane | 5.0 |
| Sorbitan sesquioleic acid ester | 4.0 |
| Polyoxyethylene(20 mol)sorbitan monooleic acid ester | 1.0 |
| Propylene glycol | 7.0 |
| Unicellularized iris rhizome (freeze-dried product) | 5.0 |
| Sodium hydrosulfite | 0.01 |
| Ethylparabenzoate | 0.3 |
| Perfume | q.s. |
| Purified water | Balance |

Method of Preparation

The polypropylene glycol was added to the purified water which was then heated and held at 70° C. (aqueous phase). Separate from this, the other ingredients were mixed and heated to melt and held at 70° C. (oil phase). The oil phase was gradually added to the aqueous phase while stirring and a homomixer was used to homogeneously emulsify the two. After the emulsification, the mixture was cooled to 30° C. with vigorous stirring to obtain the desired emulsion.

Example C6

Gel

|  | wt % |
|---|---|
| 95% ethyl alcohol | 10.0 |
| Dipropylene glycol | 15.0 |
| Polyoxyethylene(50 mol)oleyl alcohol ester | 2.0 |
| Carboxy vinyl polymer (brand name: Carbopol 940, made by G. F. Goodrich) | 1.0 |
| Potassium hydroxide | 0.15 |
| L-arginine | 0.1 |
| Unicellularized iris rhizome (freeze-dried product) | 7.0 |
| Sodium 2-hydroxy-4-methoxybenzophenone sulfonate | 0.05 |
| 3-sodium-2-hydrogen ethylene diamine tetraacetate | 0.05 |
| Methylparabenzoate | 0.2 |
| Perfume | q.s. |
| Purified water | Balance |

Method of Preparation

The Carbopol 940 was homogeneously dissolved in the purified water (aqueous phase). On the other hand, the unicellularized aloe, polyoxyethylene(50 mol)oleyl alcohol ether were dissolved in the 95% ethanol and added to the aqueous phase. Next, the other ingredients were added to the aqueous phase, then the mixture was neutralized and thickened by the potassium hydroxide and the L-arginine to obtain the desired gel.

According to the present invention, there is provided a cosmetic composition in which is formulated a unicellularized plant capable of exhibiting the features of the plant which is unicellularized, including features which remain just potential in extracts etc of the plant, to the maximum extent in an external skin treatment composition. Further, there is provided an external skin treatment composition other than a cosmetic composition which utilizes the superior characteristics as a medicine of the unicellularized plant.

What is claimed is:

1. An external skin treatment composition comprising:

substantially intact unicellularized plant cells obtained from a multicellular plant by enzymatic treatment with an enzyme selected from the group consisting of polygalacturonase obtained from *Aspergillus niger* or *Rhizopus sp.*, pectinase obtained from *Aspergillus niger* or *Rhizopus sp.*, pectin lyase obtained from *Aspergillus sp.*, and pectolyase obtained from *Aspergillus japonicus;* and a cosmetically acceptable carrier thereof.

2. An external skin treatment composition as claimed in claim 1, wherein said unicellularized plant is unicellularized carrot.

3. An external skin treatment composition as claimed in claim 1, wherein said unicellularized plant is unicellularized aloe.

4. An external skin treatment composition as claimed in claim 1, wherein said unicellularized plant is unicellularized Freesia.

5. An external skin treatment composition as claimed in claim 1, wherein said unicellularized plant is unicellularized iris rhizome.

6. An external skin treatment composition as claimed in claim 1, wherein said external skin treatment composition is a cosmetic composition.

7. An external skin treatment composition as claimed in claim 1, wherein said enzymatic treatment is carried out by selectively breaking down intercellular substances of a plant.

8. The external skin treatment composition as claimed in claim 1, wherein said Aspergillus sp. is selected from the group consisting of *Aspergillus niger* and *Aspergillus japonicus.*

* * * * *